US005633436A

United States Patent [19]
Wandelt

[11] Patent Number: 5,633,436
[45] Date of Patent: May 27, 1997

[54] FEEDCROPS ENRICHED IN SULFUR AMINO ACIDS AND METHODS FOR IMPROVEMENTS

[75] Inventor: Christine I. Wandelt, Ardentown, Del.

[73] Assignee: E. I. Du Pont de Nemours and Company, Wilmington, Del.

[21] Appl. No.: 321,080

[22] Filed: Oct. 11, 1994

Related U.S. Application Data

[63] Continuation of Ser. No. 129,721, Sep. 30, 1993, abandoned, which is a continuation-in-part of Ser. No. 29,339, Mar. 2, 1993, abandoned.

[51] Int. Cl.$^6$ .................. A01H 5/00; C12N 15/29; C12N 15/82
[52] U.S. Cl. .................. 800/205; 800/255; 800/DIG. 17; 800/DIG. 26; 536/23.6; 536/24.1; 435/69.1; 435/172.3; 435/320.1; 435/415; 435/419
[58] Field of Search .................. 800/205, 255, 800/DIG. 17, DIG. 26; 536/23.1, 24.1, 23.6; 435/69.1, 172.3, 240.4, 320.1, 240.49, 240.5, 240.51

[56] References Cited

U.S. PATENT DOCUMENTS 5,215,912 6/1993 Hoffmann .................. 435/240.4

FOREIGN PATENT DOCUMENTS 9214882 9/1992 WIPO .

OTHER PUBLICATIONS

Altenbach, S.B. et al, "Manipulation of Methionine–Rich Protein Genes in Plant Seeds", *Trends in Biotechnology*, 8(6), 155–160 (1990).
Kirihara, J.A. et al, "A Transgenic Corn Line with Altered Levels of a High–Methionine Storage Protein", *J. Cell. Biochem. Suppl.*, vol. 16F, p. 225, Abstract No. Y304 (1992).
Phillips et al., *Cereal Chem.*, 62, 213–218, 1985.
Pedersen et al, *J. Biol. Chem.*, 261, 6279–6284, 1986.
Kirihara et al., *Mol. Gen. Genet.*, 21, 477–484, 1988.
Masumura et al, *Plant Mol. Biol.*, 12, 123–130, 1989.
Axtell, J.D. (1981) In: Plant Breeding II (Frey, ed.) The Iowa State University Press, Ames Iowa Chapter 10, pp. 365–414.
Altenbach et al. Jan. 1992. Plant Mol. Biol. 18:235–245.
Ohtani et al. 1991. Plant Mol. Biol. 16:117–128.
Keith et al. 1986. EMBO J. 5:2419–2425.
Gelvin. 1987. Plant Mol. Biol. 8: 355–359.
Hoffman et al. 1987. Embo J. 6: 3213–3221.
Kirihara et al. 1988. Gene 71: 359–370.

*Primary Examiner*—David T. Fox
*Assistant Examiner*—Elizabeth F. McElwain

[57] ABSTRACT

There is provided a chimeric gene and a method to increase the seed methionine content in plants. The chimeric gene is capable of transforming plants, particularly rapeseed and soybean, to overexpress a methionine-rich maize seed storage protein in seeds. There is also provided the plants and seeds containing the chimeric gene.

16 Claims, 6 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: SM56
        ( B ) LOCATION: 1..30
        ( D ) OTHER INFORMATION: /note="synthetic oligomer"

( x i ) SEQUENCE DESCRIPTION: SEQ ID NO:1:

ATGGCAGCCA AGATGCTTGC ATTGTTCGCT ( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: CFC88
        ( B ) LOCATION: 1..30
        ( D ) OTHER INFORMATION: /note="synthetic oligomer"

( x i ) SEQUENCE DESCRIPTION: SEQ ID NO:2:

TTCTATCTAG AATGCAGCAC CAACAAAGGG ( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: OCW11
        ( B ) LOCATION: 1..18
        ( D ) OTHER INFORMATION: /note="SYNTHETIC OLIGOMER"

( x i ) SEQUENCE DESCRIPTION: SEQ ID NO:3:
        GCTGCAACAG CAGTTACC        18

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: OCW12
        ( B ) LOCATION: 1..23
        ( D ) OTHER INFORMATION: /note="SYNTHETIC OLIGOMER"

( x i ) SEQUENCE DESCRIPTION: SEQ ID NO:4:
        CGCCACTATC ATGACCCATA TTC        23

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: OCW47
        ( B ) LOCATION: 1..31
        ( D ) OTHER INFORMATION: /note="SYNTHETIC OLIGOMER"

( x i ) SEQUENCE DESCRIPTION: SEQ ID NO:5:
        CAACCCTTTG TTGGATCCGC ATTCTAGATA G ( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: OCW70
        ( B ) LOCATION: 1..19
        ( D ) OTHER INFORMATION: /note="SYNTHETIC

OLIGOMER"

( x i ) SEQUENCE DESCRIPTION: SEQ ID NO:6:

GATCAGAAAA AGACGAACT                                    19

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: OCW71
        ( B ) LOCATION: 1..19
        ( D ) OTHER INFORMATION: /note="SYNTHETIC
            OLIGOMER"

( x i ) SEQUENCE DESCRIPTION: SEQ ID NO:7:

TCTTTTTCTG CTTGAGATC                                    19

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: OCW98
        ( B ) LOCATION: 1..19
        ( D ) OTHER INFORMATION: /note= "SYNTHETIC OLIGOMER"

( x i ) SEQUENCE DESCRIPTION: SEQ ID NO:8:

CCATTGGGTA CCATGAACC                                    19

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i i ) HYPOTHETICAL: No ( i v ) ANTI-SENSE: No ( i x ) FEATURE:
        ( A ) NAME/KEY: OCW99
        ( B ) LOCATION: 1..19
        ( D ) OTHER INFORMATION: /note="SYNTHETIC
            OLIGOMER"

( x i ) SEQUENCE DESCRIPTION: SEQ ID NO:9:

CATCATGCTC GGCAAGACC                                    19

FEEDCROPS ENRICHED IN SULFUR AMINO ACIDS AND METHODS FOR IMPROVEMENTS

This is a file wrapper continuation of Ser. No: 08/129,721, filed on Sep. 30, 1993, now abandoned which is a continuation-in-part of Ser. No. 08/029,339, filed on Mar. 2, 1993, now abandoned.

TECHNICAL FIELD

This invention concerns methods for improving human food and animal feed by transformation of plant cells with novel gene constructs to yield increased levels of sulfur-rich amino acids.

BACKGROUND OF THE INVENTION

Human food and animal feed derived from many grains are deficient in the sulfur amino acids, methionine and cysteine, which are required in the animal diet. In corn, the sulfur amino acids are the third most limiting amino acids, after lysine and tryptophan, for the dietary requirements of many animals. The use of soybean meal, which is rich in lysine and tryptophan, to supplement corn in animal feed diets is limited by the low sulfur amino acid content of the legume. As a result, synthetic sources of methionine need to be added to provide nutritional value to feed rations. Thus, an increase in the sulfur amino acid content of either corn or soybean would improve the nutritional quality of these mixtures and reduce the need for further supplementation through addition of more expensive methionine. Similarly the use of rapeseed (Brassica napus) meal as animal feed ingredient would be enhanced by increasing the sulfur amino acid content of the seeds.

The amino acid content of seeds is determined primarily by the storage proteins which are synthesized during seed development and which serve as a major nutrient reserve following germination. The quantity of protein in seeds varies from about 10% of the dry weight in cereals to 20–40% of the dry weight of legumes. In many seeds the storage proteins account for 50% or more of the total protein.

Efforts to improve the sulfur amino acid content of crops through plant breeding have met with limited success on the laboratory scale and no success commercially. A mutant corn line which had an elevated whole-kernel methionine concentration was isolated from corn cells grown in culture by selecting for growth in the presence of inhibitory concentrations of lysine plus threonine (Phillips et al., Cereal Chem., 62:213–218 (1985)). However, agronomically-acceptable cultivars have not yet been derived and commercialized from this line.

Because of their abundance plant seed storage proteins were among the first proteins to be isolated. Only recently, however, have the amino acid sequences of some of these proteins been determined with the use of molecular genetic techniques. These techniques have also provided information about the genetic signals that control the seed-specific expression and the intracellular targeting of these proteins.

A number of sulfur-rich plant seed storage proteins have been identified and their corresponding genes have been isolated. A gene in corn for a 15 kD zein protein containing 11% methionine and 5% cysteine (Pedersen et al., J. Biol. Chem., 261:6279–6284 (1986)) and a gene for a 10 kD zein protein containing 22% methionine and 3% cysteine have been isolated (Kirihara et al., Mol. Gen. Genet., 21:477–484 (1988); Kirihara et al., Gene, 71:359–370 (1988)). From rice a gene coding for a 10 kD seed prolamin containing 19% methionine and 10% cysteine has been isolated (Masumura et al., Plant Mol. Biol., 12:123–130 (1989)). A high sulfur zein (HSZ) seed storage protein, related but distinct in structure to the 10 kD zein protein, was described by Chui et at. ((1992) WO92/14822).

There have been several reports on the expression of seed storage protein genes in transgenic plants. The high sulfur 2S albumin from Brazil nut protein has been expressed in rapeseed (Brassica napus) seeds at a level that resulted in an up to 33% increase in the level of methionine of the salt-extractable seed protein fraction (Altenbach et al., Plant Mol. Biol., 18:235–245 (1992)).

To date, there are no reports of the transfer of the monocotylodonous 10 kD zein gene into and its expression in dicotyledonous plant species such as tobacco, Brassica napus, soybean, sunflower, Arabidopsis, etc.

In order to increase the sulfur amino acid content of seeds it would be useful to develop a method to express a gene coding for a seed storage protein that is rich in the sulfur-containing amino acid, methionine, resulting in high levels of methionine in the seeds of transformed plants. It would be desirable for the storage protein to be compatible with those of the target crop plant and thus have no detrimental effect on seed development. Furthermore, it would be desirable that the protein come from a source that is generally regarded as safe for human food and animal feed. Crop plants obtained by this method would be valuable as sources of sulfur amino acid enriched meal.

SUMMARY OF THE INVENTION

The subject matter of the invention includes an isolated chimeric gene containing the following elements operably linked in a 5' to 3' orientation: (a) a dicotyledonous seed-specific promoter, (b) an intracellular localization sequence, (c) the maize 10 kD zein coding region, and (d) a 3' non-coding region: wherein said chimeric gene causes an increase in total seed methionine in plant cells in which the gene is expressed as compared to untransformed plant cells. Preferred 5' seed specific regulatory sequences are a bean β-phaseolin promoter, more specifically a bean β-phaseolin promoter comprising the bean β-phaseolin 5' untranslated leader region and having the 410 bp of nucleic acid sequence located directly upstream of the bean β-phaseolin transcription initiation site. The preferred 3' seed-specific regulatory sequence is a bean β-phaseolin 3' non-coding region. The preferred intracellular localization sequence for use in the chimeric gene is an amino-terminal signal peptide sequence, with the most preferred being the 10 kD zein amino-terminal signal peptide sequence.

The subject matter of the invention includes a dicotyledonous plant transformed with at least one copy of the claimed chimeric gene, with the preferred plant being a rapeseed or soybean plant. Seeds obtained from the plants are also provided.

The subject matter of the invention includes a method for increasing the sulfur amino acid content of dicotyledonous plants comprising:

(a) transforming a plant cell with a chimeric gene containing the following elements operably linked in a 5' to 3' orientation: (a) a dicotyledonous seed-specific promoter, (b) an intracellular localization sequence, (c) the maize 10 kD zein coding region, and (d) a 3' non-coding region: wherein said chimeric gene causes an increase in total seed methionine in plant cells in which the gene is expressed as compared to untransformed plant cells;

3

(b) growing fertile, sexually mature plants from the transformed plant cell; and (c) selecting progeny seed from the fertile plants of step (b) for increased levels of total seed methionine relative to dicotyledonous plant cells of the same type as those transformed in step (a) but not containing the chimeric gene.

In a preferred embodiment, the method encompasses increases in the level of total seed methionine in rapeseed relative to seed from untransformed rapeseed from 29% to 232% as compared with *Brassica napus* (cv. Westar) as untransformed control with 0.76 grams methionine per 100 grams of defatted seed meal.

The preferred embodiment also encompasses rapeseed plants wherein the polypeptide accumulates to levels from 1% to 8% of total extractable seed protein.

BRIEF DESCRIPTION OF THE SEQUENCE DESCRIPTIONS

The invention can be more fully understood from the following detailed description, the accompanying drawings, and the Sequence Descriptions which form a part of this application. The Sequence Descriptions contain the three letter codes for amino acids as defined in 37 C.F.R. 1.822 which are incorporated by reference herein.

SEQ ID NOS: 1 and 2 were used in Example 1 to PCR amplify the 10 kD zein coding region from genomic maize DNA.

SEQ ID NO: 3 was used in Example 1 to carry out the mutagenesis of the 10 kD zein gene.

SEQ ID NO: 4 was used in Example 1 to introduce a BspHI site at the signal peptide recognition site of the 10 kD zein gene by site-directed in vitro mutagenesis.

SEQ ID NO: 5 was used in Example 3 to introduce a BamHI site 11 nucleotides upstream of the 10 kD zein translation termination codon by site-directed in vitro mutagenesis.

SEQ ID NOS: 6 and 7 in Example 3 represent the oligonucleotide pair coding for the ER retention signal that was inserted at the carboxy-terminus of the 10 kD zein gene.

SEQ ID NOS: 8 and 9 were used in Example 4 for the analysis of plants transformed with 10 kD zein gene constructs.

DETAILED DESCRIPTION OF THE INVENTION

Figure 1:
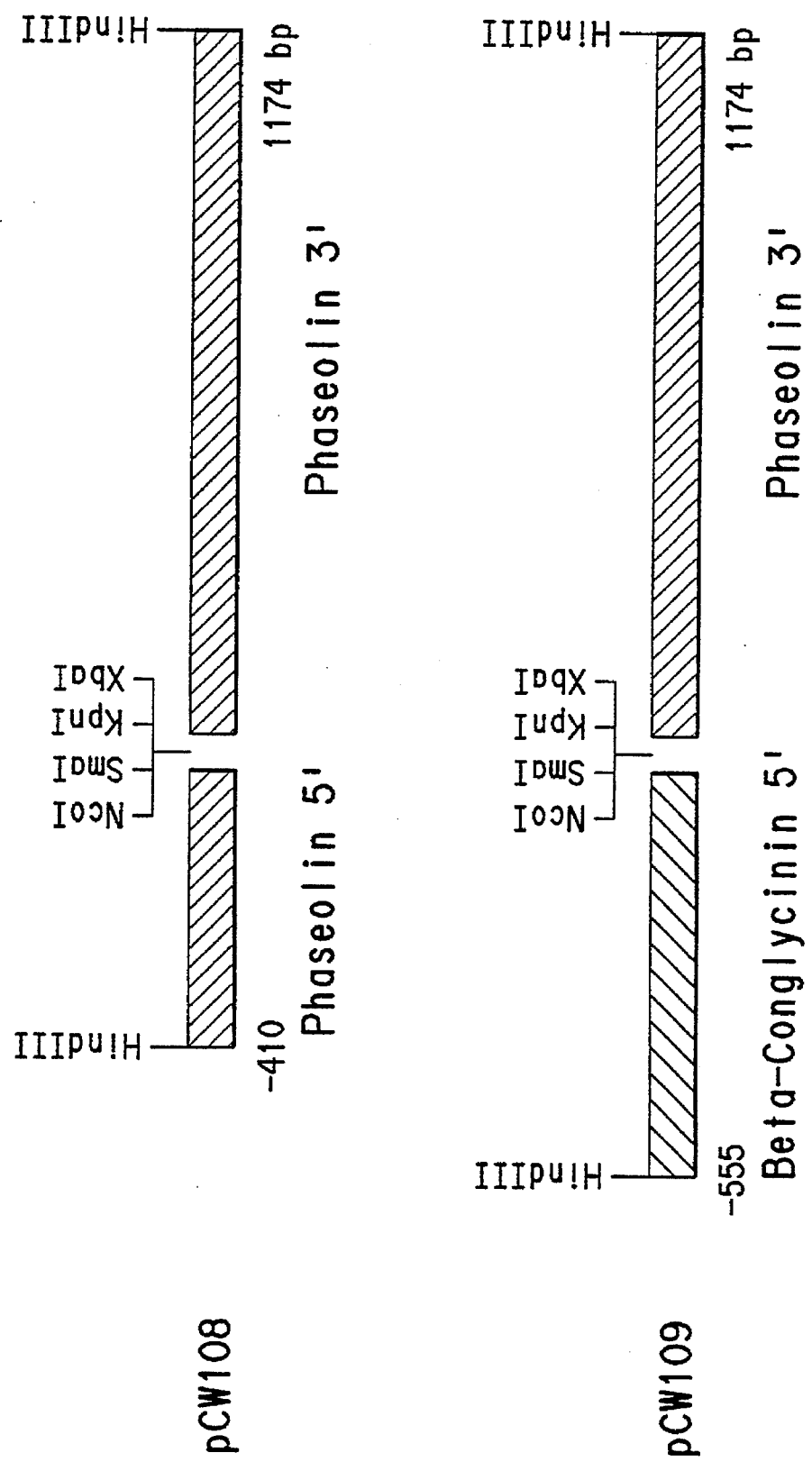
FIG. 1 shows schematically the seed specific expression cassettes pCW108 and pCW109 that were used in Example 3 for the construction of chimeric genes for expression of 10 kD zein in *Brassica napus*.

The present invention describes a novel chimeric gene comprising the monocotyledonous 10 kD zein coding region and a dicotyledonous seed-specific promoter region. The gene is capable of causing an increase in total seed methionine when expressed in a transgenic dicotyledonous plant and thus improves the nutritional quality of the seeds, particularly of rapeseed, sunflower, soybean and other legumes.

The increase in methionine content of the seed will be determined by: (1) the level of expression of the chimeric gene in the transformed crop, which depends, in part, upon the seed-specific expression signals used and on the number of copies of the gene inserted, (2) the percentage of methionine residues in the seed storage protein coding region, (3) the stability of the introduced protein in the seed of the transformed crop plant, which depends, in part, upon its proper processing, intracellular targeting, assembly into higher-order structures in some cases, and ability to withstand dessication, and (4) the compatibility of the introduced protein with the native seed proteins of the transformed crop. A transgenic rapeseed (*Brassica napus* cv. Westar) plant which distinguishes itself from an untransformed Westar plant by an increase in total methionine levels in mature seeds of 102% illustrates the effect of the chimeric gene in dicotyledonous plants. A comparable effect based on the described chimeric gene might be achieved in transgenic soybean seed as well due to the similarity of rapeseed and soybean embryos as oil and protein storage organs.

DEFINITIONS

In the context of this disclosure, a number of terms shall be utilized.

As used herein, the term "nucleic acid" refers to a large molecule which can be single-stranded or double-stranded, composed of monomers (nucleotides) containing a sugar, phosphate and either a purine or pyrimidine. A "nucleic acid fragment" or "nucleic acid sequence" is a fraction of a given nucleic acid molecule. As used herein the term "gene" refers to a nucleic acid fragment that expresses a specific protein, including regulatory sequences preceding (5' non-coding, 5' untranslated leader) and following (3' non-coding) the coding region. "Chimeric" gene refers to a gene comprising heterogeneous regulatory and coding sequences.

"Coding sequence" refers to a DNA sequence that codes for a specific protein and excludes the non-coding sequences. Depending on the protein the coding region can include intracellular localization sequences, such as an amino-terminal signal peptide, such as a signal peptide and a vacuolar targeting sequence, such as a signal peptide and an Endoplasmic Reticulum retention sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a double-stranded DNA that is complementary to and derived from mRNA. "Transcription initiation site" refers to a nucleotide in the 5' flanking region of a gene that specifies the initiation of the RNA polymerase-catalyzed transcription of that gene.

"Regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell.

These nucleotide sequences include a promoter sequence, a 5' untranslated leader sequence, a transcription termination sequence, and a polyadenylation sequence.

"Promoter" refers to a DNA sequence in a gene, usually upstream (5') to its coding sequence, which controls the expression of the coding sequence by providing the recognition for RNA polymerase and other factors required for proper transcription. A promoter may also contain DNA sequences that are involved in the binding of protein factors which control the effectiveness of transcription initiation in response to physiological or developmental conditions. A promoter may also contain enhancer elements.

An "enhancer" is a DNA sequence which can stimulate promoter activity. It may be an innate element of the promoter or a heterologous element inserted to enhance the level and/or tissue-specificity of a promoter. "Organ-specific" or "development-specific" promoters (e.g., "seed-specific promoter") as referred to herein are those that direct gene expression almost exclusively in specific organs, such as leaves or seeds, or at specific development stages in an organ, such as in early or late embryogenesis, respectively.

The term "expression", as used herein, is intended to mean the production of the protein product encoded by a gene. "Overexpression" or "overproduction" refers to the production of a gene product in transgenic organisms that exceeds levels of production in normal or non-transformed organisms.

The "3' non-coding sequences" refers to the DNA sequence portion of a gene that contains a transcription termination signal, polyadenylation signal, and any other regulatory signal capable of affecting mRNA processing or gene expression. The polyadenylation signal is usually characterized by affecting the addition of polyadenylic acid tracts to the 3' end of the mRNA precursor.

The "5' non-coding sequences" refers to the DNA sequence portion of a gene that contains a promoter sequence and a 5' untranslated leader sequence.

The "5' untranslated leader sequence" refers to that DNA sequence portion of a gene between the promoter and coding sequence that is transcribed into RNA and is present in the fully processed mRNA upstream (5') of the translation start codon. The 5' untranslated leader sequence may affect processing of the primary transcript to mRNA, mRNA stability or translation efficiency.

"Intracellular localization sequence" refers to a nucleotide sequence that encodes an intracellular targeting signal. An "intracellular targeting signal" is an amino acid sequence which is translated in conjunction with a protein and directs it to a particular sub-cellular compartment. "Signal peptide" (SP) refers to the amino terminal extension of a polypeptide, which is translated in conjunction with the polypeptide forming a precursor peptide and which is required for its entrance into the secretory pathway. The term "signal peptide sequence" refers to a nucleotide sequence that encodes the signal peptide. "Endoplasmic reticulum (ER) retention signal" refers to a carboxy-terminal extension of a polypeptide, which is translated in conjunction with the polypeptide and causes a protein that enters the secretory pathway to be retained in the ER. "ER retention signal sequence" (ER) refers to a nucleotide sequence that encodes the ER retention signal. "Vacuolar targeting signal" refers to amino-terminal, internal or carboxy-terminal peptide sequence, which is translated in conjunction with the polypeptide and causes a protein that enters the secretory pathway to be transported through the Golgi compartment to the vacuole. "Vacuolar targeting sequence" refers to the nucleotide sequence that encodes the vacuolar targeting signal.

"Meal" refers to the defatted, hexane-extracted fraction of the seed.

"Seed components" refers to fractions of the seed and products obtained from the processing of such seed including meal, oil, and protein.

"Total seed methionine" refers to the amount of methionine that can be extracted from either non-defatted or from defatted seed meal and includes free methionine and protein-bound methionine.

"Total seed protein" refers to the amount of protein that can be extracted from defatted or non-defatted seed meal using aqueous and/or alcoholic solutions.

"Transformation" herein refers to the transfer of a foreign gene into the genome of a host organism and its genetically stable inheritance. Examples of methods of plant transformation include Agrobacterium-mediated transformation and accelerated-particle or "gene gun" transformation technology.

"Multiple copies" refers to the stable integration of a foreign gene into the genome of a host organism at a single locus in tandem or inverted arrays or the integration of a foreign gene into the genome of a host organism at multiple loci as single copy and/or in tandem or inverted arrays.

Recombinant DNA technology offers the potential for increasing the sulfur amino acid content of crop plants. Particularly useful technologies are: (a) methods for the molecular cloning and in vitro manipulation of genes (see Sambrook et al., Molecular Cloning: a Laboratory Manual, Cold Spring Harbor Laboratory Press (1989)), (b) introduction of genes via transformation into agriculturally-important crop plants such as soybean (Chee et al., Plant Physiol., 91:1212–1218 (1989); Christou et al., Proc. Nat. Acad. Sci U.S.A., 86:7500–7504 (1989); Hinchee et al., Biotechnology, 6:915–922 (1989); EPO publication 0301 749 A2) and rapeseed (De Block et al., Plant Physiol., 91:694–701 (1989)), and (c) seed-specific expression of introduced genes in transgenic plants (see Goldberg et al., Cell 56:149–160 (1989); Thompson and Larkins, BioEssays, 10:108–113 (1989)).

Isolation of the 10 kD Zein Gone and its Expression in *E. coli*

The aim of the present invention was to increase the sulfur content of rapeseed (*Brassica napus*) soybean, sunflower, and other dicotyledonous seeds via introduction of the 10 kD zein gone with a methionine content of 22%, which belongs to the prolamin group of maize seed storage proteins and accumulates in protein bodies of the maize endosperm cells. To date, there are no reports of the transfer of the monocotylodonous 10 kD zein gene into and its expression in dicotyledonous plant species such as tobacco, *Brassica napus*, etc. The 10 kD zein gene has been shown to be overexpressed in a maize line selected via breeding (Kirihara et al., Mol. Gem Genet., 211:477–484 (1988)) and to be expressed in a maize line where it has been introduced via genetic engineering (see publication WO91/10725). There are only few reports on the efficient expression of the maize seed storage proteins, the zeins, in seeds of transgenic dicotyledonous plants. The so-called alpha zeins which comprise the 19 kD and 22 kD class of the maize prolamins accumulate to 0.005% of total seed protein in transgenic tobacco when placed under the control of the dicotyledonous bean seed specific phaseolin promoter (Ohtani et al., Plant Mol. Biol., 16:117–128 (1991); Williamson et al., Plant Phys., 88:1002–1007 (1988)). When placed under the control of the Cauliflower Mosaic Virus 35S promoter neither a 19 kD nor a 22 kD zein protein could be detected in embryos of mature tobacco seeds, although both proteins were present in endosperm tissue at levels up to 0.1% of ethanol-soluble proteins (Schemthaner et al.(1988) EMBO J. 7:1249–1255). In contrast, the 15 kD zein, another representative of the endosperm specific maize prolamins, under the control of the dicotyledonous bean seed specific phaseolin promoter can be expressed to levels of 1.6% of total tobacco seed protein (Hoffman et al., EMBO J., 6:3213–3221. (1987)). The gene of this invention, the 10 kD zein gene does not show any similarity on amino acid and nucleotide sequence level with the 15 kD zein, but shares sequence similarity in its signal peptide with the alpha zeins (Kirihara et al., Gene, 71:359–370 (1988)) and co-localizes with the alpha zeins at the core of the endosperm protein body after its synthesis on the rough endoplasmic reticulum (Lending and Larkins, The Plant Cell, 1:1011–1023 (1989); Esen and Stetler, American J. Botany, 79:243–248 (1992))

The previously published maize 10 kD zein gene (Kirihara et al., Gene, 71:359–370 (1988)) has been cloned from a maize genomic DNA library. The preferred constructs for expression of the 10 kD zein gene in *E. coli* was a signal peptide deletion mutant under the control of the bacteriophage T7 promoter (Rosenberg et al., Gene, 56:125–135 (1987)) as described in Examples 1 and 2. The 10 kD zein with its oval amino-terminal signal peptide could be used as well instead of the signal peptide deletion mutant. Due to the very hydrophobic nature of the 10 kD zein inclusion bodies framed in the *E. coli* cells overexpressing the 10 kD zein, 10 kD which accumulated in the inclusion bodies could easily be extracted with 70% 2-propanol in the presence of beta-mercaptoethanol to yield almost pure 10 kD zein protein. This protein isolation and purification scheme was used to isolate 10 kD zein in sufficient quantities to immunize rabbits and goat to generate polyclonal antibodies in rabbit and goat. Many other microbial expression vectors have been described in the literature. One skilled in the art could make use of any of these to construct 10 kD zein expression vectors. These 10 kD zein expression vectors could then be introduced into appropriate microorganisms via transformation to provide a system for high level expression of 10 kD zein.

Chimeric Gene Constructs For Expression of 10 kD Zein in Dicotyledonous Plants

The expression of foreign genes in plants is well established (De Blaere et al., Meth. Enzymol., 143:277–291 (1987)). Proper levels of expression of 10 kD zein may require the use of different chimeric expression cassettes utilizing different promoters. Particularly preferred among the higher plants and the seeds derived from them are rapeseed, soybean, pea and other legumes, sunflower, etc. The source of the promoter chosen to drive the expression of the coding sequence is not critical as long as it has sufficient transcriptional activity to accomplish the invention by expressing 10 kD zein in the desired host tissue. Preferred promoters are those that allow expression of the protein, specifically in seeds. Examples of seed-specific promoters include, but are not limited to the promoters of seed storage proteins. The seed storage proteins are strictly regulated, being expressed almost exclusively in seeds in a highly organ-specific and stage specific manner (Higgins et al., Ann. Rev. Plant Physiol., 35:191–221 (1984); Goldberg et al., Cell, 56:149–160 (1989); Thompson et al., BioEssays, 10:108–113 (1989)). Moreover, different seed storage proteins may be expressed at different stages of seed development.

There are currently numerous examples for seed-specific expression of seed storage protein genes in transgenic dicotyledonous plants. These include genes from dicotyledonous plants for bean β-phaseolin (Sengupta-Gopalan et al., Proc. Natl. Acad. Sci. USA, 82:3320–3324 (1985); Hoffman et al., Plant Mol. Biol., 11:717–729 (1988)), bean lectin (Voelker et al., EMBO J., 6:3571–3577 (1987)), soybean lectin (Okamuro et al., Proc. Natl. Acad. Sci. USA, 83:8240–8244 (1986)), soybean kunitz trypsin inhibitor (Perez-Grau et al., Plant Cell, 1:095–1109 (1989)), soybean β-conglycinin (Beachy et al., EMBO J., 4:3047–3053 (1985); Barker et al., Proc. Natl. Acad. Sci. USA, 85:458–462 (1988); Chen et al., EMBO J., 7:297–302 (1988); Chen et al., Dev. Genet., 10:112–122 (1989); Naito et al., Plant Mol. Biol., 11:109–123 (1988)), pea vicilin (Higgins et al., Plant Mol. Biol., 11:683–695 (1988)), pea convicilin (Newbigin et al., Planta, 180:461 (1990)), pea legumin (Shirsat et al., Mol. Gen. Genetics, 215:326 (1989)); rapeseed napin (Radke et al., Theor. Appl. Genet., 75:685–694 (1988); Stayton et al., Aus. J. Plant Phys., 18:507–517 (1991)). Moreover, promoters of seed-specific genes, operably linked to heterologous coding sequences in chimeric gene constructs, also maintain their temporal and spatial expression pattern in transgenic plants. Such examples include *Arabidopsis thaliana* 2S seed storage protein gene promoter to express enkephalin peptides in *Arabidopsis* and *B. napus* seeds (Vandekerckhove et al., Bio/Technology, 7:929–932 (1989)), bean lectin and bean β-phaseolin promoters to express luciferase (Riggs et al., Plant Sci., 63:47–57 (1989)).

Of particular use in the expression of the nucleic acid fragment of the invention will be the promoters from several extensively characterized soybean seed storage protein genes such as those for the Kunitz trypsin inhibitor (Jofuku et al., Plant Cell, 1:1079–1093 (1989); Perez-Grau et al., Plant Cell, 1:1095–1109 (1989)), glycinin (Nielson et al., Plant Cell, 1:313–328 (1989)), β-conglycinin (Harada et al., Plant Cell, 1:415–425 (1989)); and from the extensively characterized bean seed storage protein gene for phaseolin (Doyle et al., J. Biol. Chem., 261:9228–9238 (1986)). The β-phaseolin promoter has been characterized in more detail regarding regulatory domains required for tissue and developmental specific expression (Burow et al., Plant J., 2:537–548 (1992); Bustos et al., Plant Cell, 1:839–853 (1989); Bustos et al., EMBO J., 10:1469–1479 (1991); Kawagoe and Murai, Plant J., 2:927–936 (1992)).

Especially preferred among the seed storage protein promoters is a version of the bean β-phaseolin promoter encompassing 410 bp upstream of the transcription initiation site and a version of the soybean β-conglycinin α'-subunit encompassing 550 bp upstream of the transcription initiation site (see publication WO91/13993 and Doyle et al., J. Biol. Chem., 261:9228–9238 (1986)). One can also envision a modified β-phaseolin promoter with its silencer regions deleted (Bustos et al., EMBO J., 10:1469–1479 (1991)) as a promoter which might confer expression levels up to 100% higher than the unmodified full length β-phaseolin promoter. In tobacco transformed with β-phaseolin promoter deletion constructs a minimum of 795 bp upstream of the transcription initiation site is necessary for 100% promoter activity in seeds; a promoter fragment encompassing only 418 bp upstream of the transcription initiation site will give 20% promoter activity in transgenic tobacco seeds (Bustos et al., EMBO J., 10:1469–1479 (1991)).

The introduction of enhancers or enhancer-like elements into other promoter constructs will also provide increased levels of primary transcription for a 10 kD zein gene to accomplish the invention. These would include viral enhancers such as that found in the 35S promoter (Odell et al., Plant Mol. Biol., 10:263–272 (1988)), enhancers from the opine genes (Fromm et al., Plant Cell, 1:977–984 (1989)), or enhancers from any other source that result in increased transcription when placed into a promoter operably linked to the nucleic acid fragment of the invention. Of particular importance is the DNA sequence element isolated from the gene for the α'-subunit of β-conglycinin that can confer 40-fold seed-specific enhancement to a constitutive promoter (Chen et al., EMBO J., 7:297–302 (1988); Chen et al., Dev. Genet., 10:112–122 (1989)). One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

Any 3' non-coding region capable of providing a polyadenylation signal and other regulatory sequences that may be required for the proper expression of the 10 kD zein coding region can be used to accomplish the invention. This would include the 3' end from any storage protein such as the 3' end of the bean β-phaseolin gene, the 3' end of the soybean β-conglycinin gene, the 3' end from viral genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/10 kD zein coding region combination to which it is operably linked. There are numerous examples in the art that teach the usefulness of different 3' non-coding regions (for example, see Ingelbrecht et al., Plant Cell, 1:671–680 (1989)).

Figure 2:
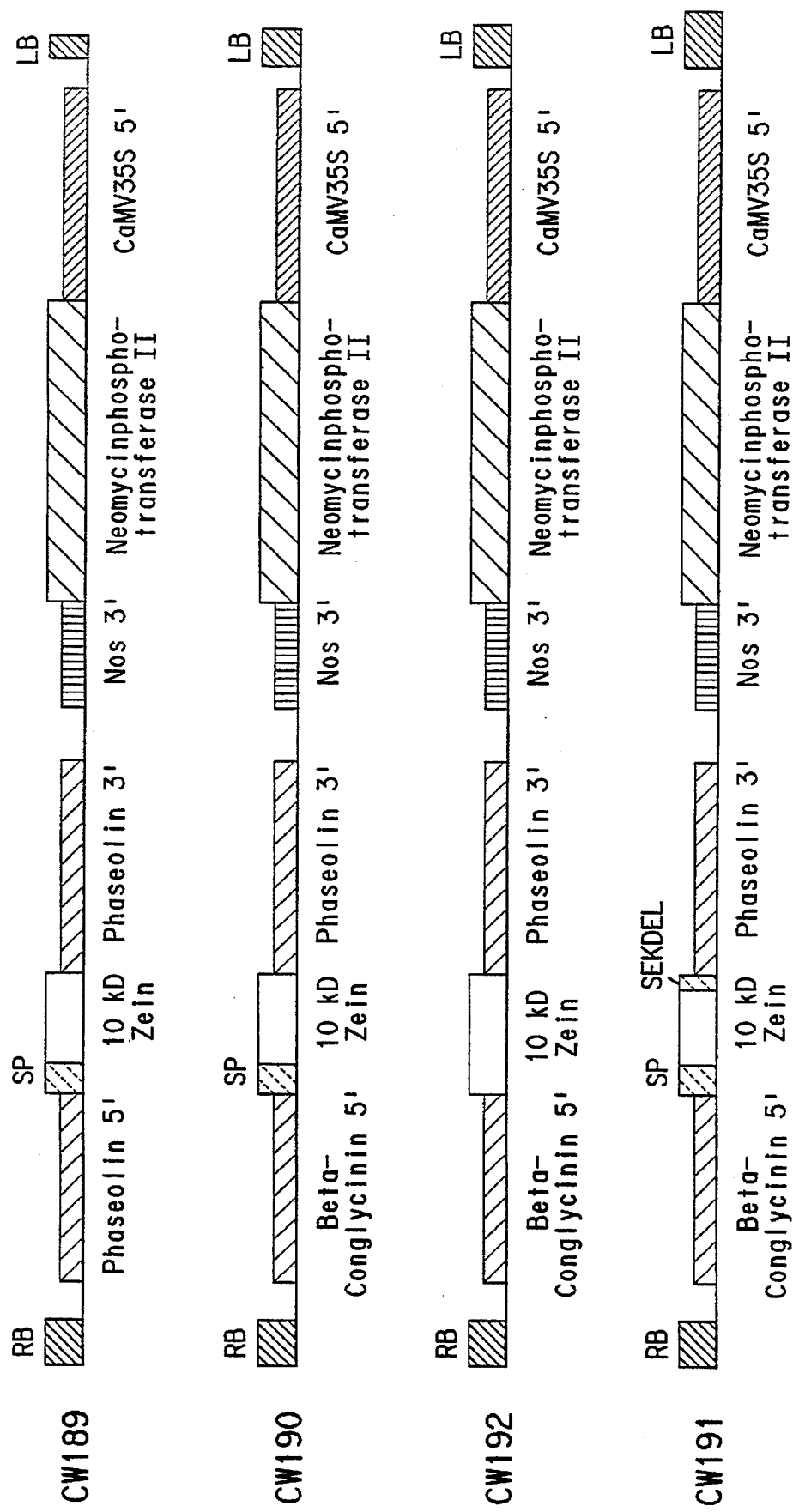
FIG. 2 shows a summary of the chimeric 10 kD zein gene constructs that were used in Example 4 to transform *Brassica napus* plants.
Figure 6:
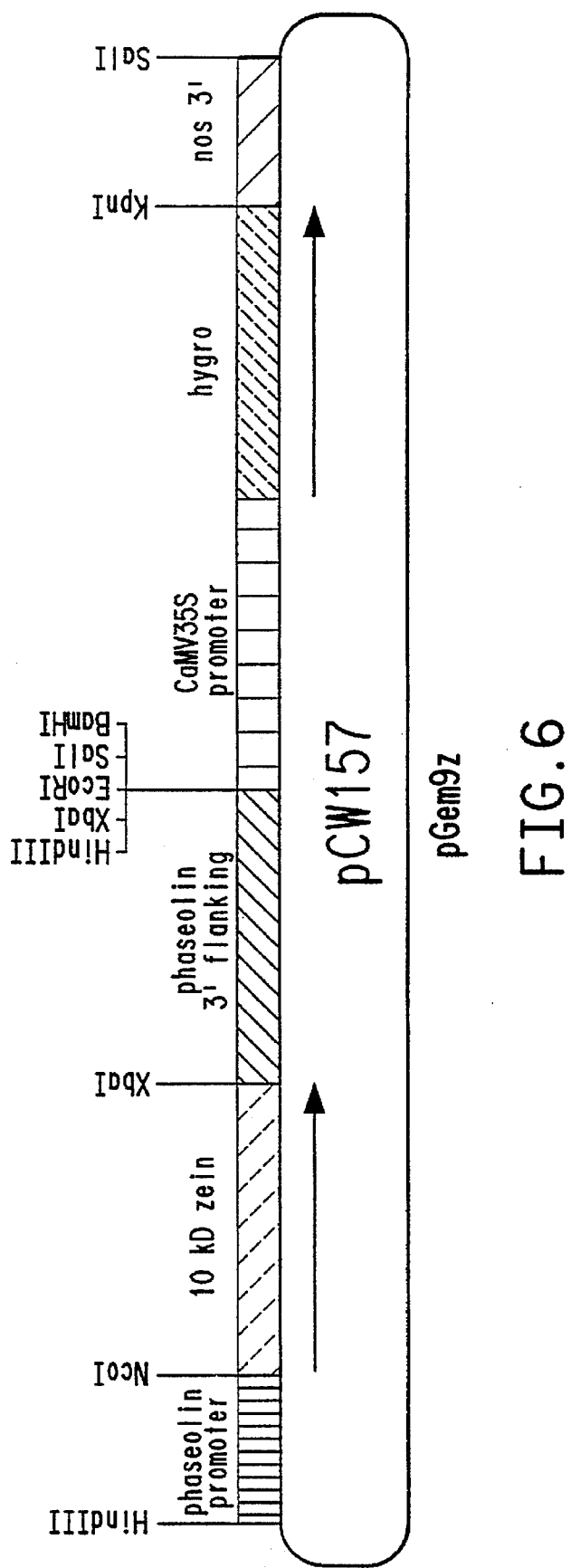
FIG. 6 shows a map of gene construct pCW157 which is described in Example 8.

In addition, the efficient expression of 10 kD zein in dicotylodonous hosts might benefit from suitable intracellular localization signals. 10 kD zein is a maize endosperm specific seed storage protein and accumulates in protein bodies that are derived from the endoplasmatic reticulum membrane (Esen and Stetler, American J. Bot., 79:243–248 (1992); Lending et al., Protoplasma, 143:51–62 (1988); Wallace et al., Biochem. Physiol. Planzen, 183:107–115 (1988); Lending and Larins, Plant Cell, 1:1011–1023 (1989)). In contrast, in dicot embryos seed storage proteins such as the soybean or pea seed storage proteins accumulate in protein bodies that are derived from the vacuole (Chrispeels, Annu. Rev. Plant Physiol. Plant Mol. Biol., 42:21–53 (1991); Chrispeels and Raikhel, Cell, 68:613–616 (1992)). The effect of this is that the intracellular localization of seed storage proteins differs significantly in maize endosperm from *Brassica napus* or soybean embryos. Correct targeting of the 10 kD zein in heterologous hosts might have a significant impact on the stability and thus on the expression levels of this protein. One can envision adding an ER retention signal carboxy-terminal to the 10 kD zein so that it will be retained in the ER and not transported to the vacuole and thus facilitate the accumulation of 10 kD zein in *Brassica napus* embryos. The highly conserved sequence Lys-Asp-Glu-Leu (KDEL) present at the carboxy-terminus of mammalian reticuloplasmins was shown to be necessary for their retention and appears to be sufficient to reduce the secretion of several secretory proteins (Munro and Pelham, Cell, 48:899–907 (1987); Zagouras and Rose, J. Cell. Biol., 109:2633–2640 (1989); Pelham, EMBO J., 7:913–918 (1988); Pelham et al., EMBO J., 7:1757–1762 (1988); Inohara et al., Proc. Natl. Acad. Sci. USA, 86:3564–3568 (1989); Hesse et al., EMBO J., 8:2453–2461 (1989); Tillman et al., EMBO J., 8:2463–2467 (1989); Akasofu et al., Nucleic Acids Res., 17:6733 (1989); Tanaka et al., Plant Mol. Biol., 16:1083–1084 (1991); Denecke et al., EMBO J., 11:2345–2355 (1992)). The addition of the KDEL sequence to the carboxy-terminus of the pea vicilin gene increased its stability in transgenic tobacco leaves by 100 fold (Wandelt et al., Plant J., 2:181–192 (1992)). It may be useful to direct the 10 kD zein to the vacuole of *Brassica napus* embryo cells by adding a vacuolar targeting signal. Short amino-, carboxy-terminal or internal interspersed amino acid domains that direct proteins to the vacuole have been identified in several plant seed storage proteins (Chrispeels and Raikhel, Cell, 68:613–616 (1992); Bednarek and Raikhel, Plant Mol. Biol., 20:133–150 (1992); Bednarek and Raikhel, Plant Cell, 3:1195–1206 (1991); Holwerda et al., Plant Cell, 4:307–318 (1992); Matsuoka et al., J. Biol. Chem., 265:19750–19757 (1990); Neuhaus et al., Proc. Natl. Acad. Sci. USA, 88:10362–10366 (1991)). Seed storage proteins enter the secretory pathway via an amino-terminal extension, the signal peptide. One could create a 10 kD zein gene lacking the signal peptide which would render the protein cytoplasmic (Chrispeels, Annu. Rev. Plant Physiol. Plant Mol. Biol., 42:21–53 (1991); Wandelt et al., Plant Molecular Biology, 2:471–478 (1991)). The following four chimeric constructs (see also Example 3) are the preferred constructs of the invention. (1) bean β-phaseolin -410 promoter/10 kD zein/bean β-phaseolin 3' flanking region; (2) soybean β-conglycinin -550 promoter/10 kD zein/bean β-phaseolin 3' flanking region; (3) soybean β-conglycinin -550 promoter/10 kD zein-SEKDEL/bean β-phaseolin 3' flanking region; (4) soybean β-conglycinin -550 promoter/SPdel-10 kD zein/bean β-phaseolin 3' flanking region. The constructs are schematically shown in FIG. 2. (The abbreviations used in FIG. 2 and FIG. 6 are as follows: "RB" refers to Right Border; "LB" refers to Left Border; "SP" refers to Signal Peptide; "NOS" refers to "Nopaline Synthase"; "CaMV" refers to Cauliflower Mosaic Virus; "SEKDEL" refers to Ser-Glu-Lys-Asp-Glu-Leu, ER Retention Signal.)

Transformation of Dicotyledonous Plants with Chimeric Gene Constructs for Expression of 10 kd Zein Various methods of introducing a DNA sequence (i.e., of transforming) into eukaryotic cells of higher plants are available to those skilled in the art (see EPO publications 0 295 959 A2 and 0 138 341 A1). Such methods include those based on transformation vectors based on the Ti and Ri plasmids of Agrobacterium spp. It is particularly preferred to use the binary type of these vectors. Ti-derived vectors transform a wide variety of higher plants, including monocotyledonous and dicotyledonous plants, such as soybean, cotton and rape (Pacciotti et al., Bio/Technology, 3:241 (1985); Byme et al., Plant Cell, Tissue and Organ Culture, 8:3 (1987); Sukhapinda et al., Plant Mol. Biol., 8:209–216 (1987); Lorz et al., Mol. Gen. Genet., 199:178 (1985); Potrykus, Mol. Gen. Genet., 199:183 (1985)).

For introduction into plants the chimeric genes of the invention can be inserted into binary vectors as described in Examples 3–6. The vectors are part of a binary Ti plasmid vector system. (Bevan, Nucl. Acids. Res., 12:8711–8720 (1984)) of *Agrobacterium tumefaciens*. Other transformation methods are available to those skilled in the art, such as direct uptake of foreign DNA constructs (see EPO publication 0 295 959 A2), techniques of electroporation (see Fromm et al., Nature (London), 319:791 (1986)) or high-velocity ballistic bombardment with metal particles coated with the nucleic acid constructs (see Klein et al., Nature (London), 327:70 (1987), and see U.S. Pat. No. 4,945,050). Once transformed, the cells can be regenerated by those skilled in the art.

Of particular relevance are the recently described methods to transform foreign genes into commercially important crops, such as rapeseed (see De Block et al., Plant Physiol., 91:694–701 (1989)), sunflower (Everett et al., Bio/Technology, 5:1201 (1987)), soybean (McCabe et al., Bio/Technology, 6:923 (1988); Hinchee et al., Bio/Technology, 6:915 (1988); Chee et al., Plant Physiol., 91:1212–1218 (1989); Christou et al., Proc. Natl. Acad. Sci USA, 86:7500–7504 (1989); EPO Publication 0 301 749 A2; Finer et al., In Vitro Cell. Dev. Biol., 27P:175–182 (1991)), and corn (Gordon-Kamm et al., Plant Cell, 2:603–618 (1990); Fromm et al., Biotechnology, 8:833–839 (1990)).

Expression of 10 kD Zein in Transgenic Dicotyledonous Plants

To assay for expression of the chimeric genes in seeds of the transformed plants, the 10 kD zein protein can be extracted, detected and quantitated immunologically by methods known to those skilled in the art. Amino acid analysis methods can be used to measure the increase in total methionine levels due to the expression of the introduced high methionine 10 kD zein gene (see Examples 5 and 6). Using these assays transgenic Brassica napus lines expressing high levels of 10 kD zein were identified. Significant increases in overall methionine levels in mature seeds (via multiple single seed or seed meal analysis) from transgenic Brassica napus lines transformed with 10 kD zein gene constructs were detected. One out of 24 plants showed an increase in total methionine of 102% (heterozygous situation) which corresponds to expression levels of 3.9% of total seed protein; 6 out of 24 plants show expression levels of 10 kD zein of 0.4 to 1% of total seed protein. Seventeen out of 24 plants show expression levels of less than 0.05% of total seed protein. This group of plants is predominantly found in lines that have been transformed with 10 kD zein genes harboring modified targeting signals (signal peptide deletion or ER retention signal addition). 10 kD zein with its own signal peptide accumulates stably in seeds of transformed Brassica napus plants. In a homozygous situation expression levels of almost 8% 10 kD zein of total seed protein might be achieved according to the single seed amino acid analysis (see FIG. 3).

Inter-transformant variability in transgenic expression as seen in the above description could be related to the copy number of the introduced genes, the site of integration and other factors. There are no examples known where a clear correlation between transgene copy number and transgene expression has been shown; there are even indications that single copies result in higher expression of the transgene (see Hobbs et al., Plant Mol. Biol., 15:851–864 (1990); and references therein). However, some examples exist wherein the highest expression levels correlate with a high gene copy number. Altenbach et al., Plant Mol. Biol., 13:513–522 (1989); Leisy et al., Plant Mol. Biol., 14:41–50 (1989)). As shown in Example 7, the gene copy number is of importance in achieving high levels of expression in transgenic Brassica napus seeds. The highest expressing plant shows integration of the transgene at at least 2 major loci with a total gene copy number of >5. One can envision constructs harboring the 10 kD zein gene under the control of seed specific promoters in tandem arrays on a binary vector to achieve higher copy numbers of the introduced gene of interest.

Canola meal is widely used in Canada for feeding poultry because of its nutritional value and availability at a price competitive with other protein supplements. The protein content of canola meal ranges from 37 to 38%. Feeding trials on the use of canola meal for broilers usually contain 10 to 20% of canola meal to supplement either wheat and/or corn, the principal grain component. Canola meal is relatively high in lysine, an essential amino acid deficient in cereal grains, and methionine, which is beneficial when fed with grains, such as maize, in which these essential amino acids are limiting. Because canola meal is considered equivalent in quality to that of soybean, an increase in the level of lysine and methionine could be an advantage in the market. One can envision the use of canola seed meal from a canola plant with an increased seed methionine content as great as 232% as a significantly improved feed supplement in the poultry industry.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

10 kD Zein Constructs for Expression in E. Coli

The coding region of time high methionine 10 kD maize seed storage protein or 10 kD zein (for sequence see Kirihara et al., Gene, 71:359–370 (1988)) was isolated from genomic maize DNA (line B85) using the polymerase chain reaction (PCR). Two oligonucleotides flanking the 10 kD zein coding region were synthesized (Applied Biosystems).

SM56 (SEQ ID NO:1)
5'-ATG GCA GCC AAG ATG CTT GCA TTG TTC GCT-3'
Met Ala Ala Lys Met Leu Ala Leu Phe Ala

CFC88 (SEQ ID NO:2)
5'-T TCT ATC TAG AATGCAGCACCAACAAAGGG-3'
Ala Phe *

The PCR reaction was preformed using a Perkin-Elmer Cetus kit according to the instructions of the vendor on a thermocycler manufactured by the same company. The PCR reaction product of 450 bp was blunt-ended with Klenow DNA polymerase, cleaved with XbaI (see underlined sequence in oligonucleotide CFC88) and subcloned into the commercially available (Pharmacia) vector pTZ18R linearized with SmaI and XbaI, yielding the plasmid pCC1. The entire coding region was sequenced (United States Biochemicals kit). The sequence deviated from the published coding sequence (Kirihara et al., Gene, 71:359–370 (1988)) in one base pair at nucleotide position 1504 of the published sequence. An A was changed to a G which resulted in the change of amino acid 123 (with the initiator methionine as amino acid 1) from Gln to Arg. It is not known if the detected mutation was generated during the PCR reaction or if this is indeed another allele of the maize 10 kD zein gene. To revert the mutation back to the published sequence the plasmid pCC1 was mutagenized by oligonucleotide-directed site-specific mutagenesis (BioRad kit, Hercules, Calif.) using oligonucleotide OCW11.

OCW11 (SEQ ID NO:3)
5'-G CTG CAA CAG CAG TTA CC-3'
   Leu Gln Gln Gln Leu

The resulting plasmid named pCW116 was sequenced to verify the reversal of the mutation (see underlined nucleotide in SEQ ID NO:3) and used as a basic construct for the chimeric genes presented in Example 3. In a second mutagenesis reaction with plasmid pCC1 and oligonucleotides OCW11 and OCW12 a BspHI site (see underlined nucleotides in SEQ ID NO:4) was created at the signal peptide recognition site (amino acids representing the amino-terminus of the mature 10 kD zein are underlined in SEQ ID NO:4).

OCW12 (SEQ. ID NO:4)
5'-C GCC ACT ATC ATG ACC CAT ATT C-3'
  Ala Thr Ser Ala Thr His Ile

Sequencing of the resulting plasmid pCW 119 confirmed the reversal of the mutation at site 1504 of the published sequence (Kirihara et al., Gene, 71:359-370 (1988)) from 5'-GCAACGGC-3' to 5'-GCAACAGC-3' and the creation of a BspHI site from 5'-CTAGTGCGA-3' to 5'-CTATCATGA-3'. To achieve high levels of expression of the mature 10 kD zein coding sequence in E. coli, the bacterial expression vector pBT430 was used. This vector is a derivative of pET-3a (Rosenberg et al., Gene, 56:125-135 (1987)) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and HindIII sites was then inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3.aM in this region, 5'-CATATGG (NdeI site underlined), was converted to 5'-CCCATGG (NcoI site underlined) in pBT430. The BspHI/HindIII fragment of plasmid pCW119 was ligated into pBT430 linearized with NcoI and HindIII (for standard cloning procedures see Sambrook et al., Molecular Cloning: A Laboratory Manual, Cold Spring Harbor Laboratory Press (1989)) resulting in plasmid pCW124. This plasmid carries only the region coding for the mature form of the 10 kD zein under the control of the bacteriophage T7 promoter.

Example 2

Overexpression of 10 kD zein in E. coli

A 10 L culture of E. coli strain BL21(DE3) (Studier et al., Methods in Enzymology, 185:60-89 (1990)) harboring the plasmid pCW124 was grown in LB medium plus ampicillin (0.1 g/L) at 37° C. under standard conditions in a BIOSTAT E (B. Brown Company). At $OD_{600 \, nm}$ of 0.7 the culture was induced with isopropylthio-β-galactoside (IPTG) to a final concentration of 0.4 mM and incubation was continued over night at 37° C. with the culture reaching a final $OD_{600 \, nm}$ of 1.0. The volume of the culture medium was reduced to 0.9 L by membrane filtration after which the cells were harvested by a final centrifugation step. The cell pellet was washed twice with 100 mL of 50 mM NaCl, 50 mM Tris-HCl, 1 mM EDTA, pH 7.5 (TEN) and frozen at –20° C. The pellet was thawed, resuspended in 50 mL of TEN including PMSF to a final concentration of 1 mM (TEN+P) and sonicated at 4° C. Cell debris was collected in a spin for 10 min at 10 krpm. The pellet (mainly inclusion bodies) was extracted 3 times with a total of 100 mL 70% 2-propanol, 0.2% β-mercaptoethanol, yielding 700 mg of greater than 95% pure 10 kD zein. Aliquots from all 3 alcoholic fractions of 10 kD zein were subjected to SDS-polyacrylamide gel electrophoresis. The predominant band visible by Coomassie Blue staining was the 10 kD zein. About four milligrams of the purified protein were sent to Hazelton Research Facility, 310 Swampridge Road, Denver, Pa. 17517, to obtain antibodies raised against 10 kD zein in rabbit and goat.

Example 3

Chimeric Gene Constructs for Expression of 10 kD Zein in Brassica Napus (cv. Westar)

Two seed-specific expression cassettes were used as a basis for chimeric gene constructs for expression of 10 kD zein in Brassica napus. The cassettes are shown schematically in FIG. 1. Cassette pCW108 contains 410 basepairs of the bean (Phaseolus vulgaris) phaseolin (β-subunit of the 7S seed storage protein) promoter starting with 5'-TGGTCTTTTGGTTCATG-3' (see sequence in Doyle et al., J. Biol. Chem., 261:9228-9238 (1986) and WO91/13993), the β-phaseolin 5' untranslated leader and the β-phaseolin 3' untranslated region of 1174 base pairs. Cassette pCW109 contains 555 basepairs of the β-conglycinin promoter (α' subunit of the 7S seed storage protein) promoter from soybean (Glycine max), the β-conglycinin 5' untranslated region and 1174 basepairs of the bean β-phaseolin 3' untranslated legion. The sequence represents an allele of the published β-conglycinin gene (Doyle et al., J. Biol. Chem., 261:9228-9238 (1986)) due to differences at 27 nucleotide positions, although none of them in a region that has been shown to be important for enhanced and tissue specific expression of this seed storage protein gene. A multiple cloning site (NcoI, SmaI, KpnI and XbaI) in cassettes pCW108 and pCW109 separates the 5' flanking region from the 3' flanking region and allows the convenient insertion of any coding region. The 10 kD zein coding region from plasmid pCW116 was inserted as a NcoI/XbaI fragment into the seed specific expression cassettes pCW108 and pCW 109 resulting in the following constructs, which are flanked by unique HindIII restriction sites: (1) pCW126: β-phaseolin 5'-10 kD zein β-phaseolin 3', and (2) pCW128: β-conglycinin 5'-10 kD zein-β-phaseolin 3'. To facilitate subcloning of the above chimeric constructs into binary Ti based vectors for plant transformation, (1) pCW 126 was digested with HindIII, which creates a restriction fragment harboring the β-phaseolin 5'-10 kD zein coding-β-phaseolin 3' chimeric gene and was ligated into pUC1318 (Kay et al., Nucl. Acids Res., 6:2778 (1987)) linearized with HindIII, resulting in plasmid pCW171. (2) Plasmid pCW128 was digested with HindIII and subcloned into the commercially available vector Bluescript SK(−) cut with HindIII resulting in plasmid pCW182. Both constructs pCW171 and pCW182 with their convenient cloning sites enable the ligation of the 10 kD zein seed specific expression cassettes into binary Ti plasmid based vectors (Bevan, Nucl. Acids. Res., 12:8711-8720 (1984)) of Agrobacterium tumefaciens. The vectors contain: (1) the chimeric gene CaMV35S/neomycin phosphotransferase/nopaline synthase (35S:NPTII:nos) as a selectable marker for transformed plant cells (Bevan et al., Nature, 304:184–186 (1983)), (2) the left and right borders of the T-DNA of the Ti plasmid (Bevan, Nucl. Acids. Res., 12:8711–8720 (1984)), (3) the *E. coli* lacZ α-complementing segment (Vieria and Messing, Gene, 19:259–267 (1982)) with unique restriction endonuclease sites for EcoR I, Kpn I, BamH I and Sal I, (4) the bacterial replication origin from the Pseudomonas plasmid pVS1 (Itoh et al., Plasmid, 11:206–220 (1984)), and (5) the bacterial neomycin phosphotransferase gene from Tn5 (Berg et al., Proc. Natl. Acad Sci. USA, 72:3628–3632 (1975)) as a selectable marker for transformed *A. tumefaciens*. Plasmid pCW171 was digested with BamHI yielding the chimeric gene fragment: β-phaseolin 5'-10 kD zein-β-phaseolin 3', which was ligated into the binary vector pZS 199 linearized with BamHI resulting in plasmid pCW189 (see FIG. 2). Plasmid pCW182 was digested with SalI and EcoRI yielding the chimeric gene β-conglycinin 5'-10 kD zein-β-phaseolin 3', which was ligated into the binary vector pZS 198 linearized with SalI and EcoRI, resulting in plasmid pCW190 (see FIG. 2). In addition, two targeting mutant constructs of 10 kD zein were: created: (1) with a deleted signal peptide sequence, and (2) with an Endoplasmic Reticulum (ER) retention signal sequence added. To obtain the signal peptide deletion mutant plasmid pCW119 (see Example 1) was digested with BspHI and XbaI and the resulting mature 10 kD zein coding sequence was ligated into the seed expression cassette pCW109 which has been linearized with NcoI and XbaI, resulting in plasmid pCW125. To facilitate further cloning of the 10 kD zein coding region under the control of the β-conglycinin promoter, the plasmid pCW125 was digested with HindIII and the β-conglycinin-10 kD zein-β-phaseolin 3' fragment was ligated into the vector pUC1318 linearized with HindIII, yielding the plasmid pCW151. In order to transfer the 10 kD zein signal peptide deletion mutant gene construct into a binary vector the plasmid pCW151 was digested with BamHI and the 10 kD zein chimeric gene was ligated into the binary vector pZS 199 linearized with BamHI, resulting in plasmid pCW192 (see FIG. 2). To add the ER retention signal sequence SerGluLysAspGluLeu (Pelham, Trends Biochem. Sci., 15:483–486 (1990)) onto the carboxy terminus of 10 kD zein, the following mutagenesis reaction was performed. The plasmid pCC 1 (see Example 1) was mutagenized using oligonucleotide OCW11 (see Example 1) and oligonucleotide OCW47.

OCW47 (SEQ ID NO:5)
5'-CAA CCC TTT GTT GGA TCC GCA TTC TAG ATAG-3'
   Gln Pro Phe Val Gly Ala Ala Phe *

Mutagenesis with OCW47 introduces a BamHI cleavage site (see underlined nucleotides in SEQ ID NO:5) 11 basepairs upstream of the 10 kD zein translation stop codon. The sequence 5'-GGTGCTGCA-3' is changed into 5'-GGATCCGCA-3'. The resulting plasmid pCW152 was sequenced to verify the introduced mutations and digested with BamHI to allow the insertion of the oligonucleotide pair OCW70 and OCW71, coding for the ER retention signal.

OCW70 (SEQ ID NO:6)
5'-GA TCA GAA AAA GAC GAA CT-3'

OCW71 (SEQ ID NO:7)
5'-T CTT TTT CTG CTT GAG ATC-3'
   Ser Glu Lys Asp Glu Leu *

The resulting plasmid was pCW173. In the next cloning step the 10 kD zein-SEKDEL mutant was inserted into the seed specific expression cassette pCW109 via NcoI and XbaI, resulting in plasmid pCW180. To ease subcloning into a binary vector the β-conglycinin 5'-10 kD zein-β-SEKDEL-phaseolin 3' chimeric gene was moved from pCW 180 as a HindIII fragment into the commercially available vector BluescriptSK(–), resulting in plasmid pCW183. Digestion of pCW183 with SalI and EcoRI allowed ligation of the chimeric β-conglycinin 5'-10 kD zein-SEKDEL-phaseolin 3' gene into the binary vector pZS 198, linearized with SalI and EcoRI. The resulting plasmid was pCW191 (see FIG. 2). As a summary of the above described chimeric constructs see FIG. 2.

Example 4

Transformation of *Brassica napus* (cv. Westar) with the chimeric gene constructs pCW189, pCW190, pCW191 and pCW192

The binary vectors containing the chimeric 10 kD zein genes were transferred by tri-parental mating (Ruvkin et al., Nature, 289:85–88 (1981)) to Agrobacterium strain LBA4404/pAL4404 (Hockema et al., Nature, 303:179–180 (1983)).

The transformed Agrobacterium strains were used to inoculate seedling pieces of *Brassica napus* cultivar "Westar" using the following procedure.

*B. napus* seeds are sterilized by stirring in 10% Chlorox, 0.1% SDS for thirty min, and then rinsed thoroughly with sterile distilled water. The seeds were germinated on sterile medium containing 30 mM $CaCl_2$ and 1.5% agar, and grown for six d in the dark at 24° C.

Liquid cultures of Agrobacterium for plant transformation were grown overnight at 28° C. in Minimal A medium containing 100 mg/L kanamycin. The bacterial cells were pelleted by centrifugation and resuspended at a concentration of $10^8$ cells/mL in liquid Murashige aud Skoog Minimal Organic medium containing 100 µM acetosyringone.

*B. napus* seedling hypocotyls were cut into 5 mm segments which were immediately placed into the bacterial suspension. After 30 min, the hypocotyl pieces were removed from the bacterial suspension and placed onto BC-12 callus medium containing 100 µm acetosyringone. The plant tissue and Agrobacteria were co-cultivated for three d at 24° C. in dim light.

The co-cultivation was terminated by transferring the hypocotyl pieces to BC-12 callus medium containing 200 mg/L carbenicillin to kill the Agrobacteria, and 25 mg/L kanamycin to select for transformed plant cell growth. The seedling pieces were incubated on this medium for three weeks at 24° C. under continuous light.

After three weeks, the segments were transferred to BS-48 regeneration medium containing 200 mg/L carbenicillin and 25 mg/L kanamycin. Plant tissue was subcultured every two weeks onto fresh selective regeneration medium, under the same culture conditions described for the callus medium. Putatively transformed calli grew rapidly on regeneration medium; as calli reached a diameter of about 2 mm, they were removed from the hypocotyl pieces and placed on the same medium lacking kanamycin.

Shoots began to appear within several weeks after transfer to BS-48 regeneration medium. As soon as the shoots formed discernable stems, they were excised from the calli, transferred to MSV-1A elongation medium, and moved to 16:8-hour photoperiod at 24° C.

Once shoots had elongated several internodes, they were cut above the agar surface and the cut ends were dipped into ROOTONE. Treated shoots were planted directly into wet METRO-MIX 350 soilless potting medium in an 8" standard pot. The pots were covered with plastic bags which were removed when the plants were clearly growing—usually after about ten days.

Plants were grown in a growthroom at 20° C. under a 16:8-hour photoperiod. They were watered three times daily with 0.5X Hoagland's Solution until they began flowering. At flowering, nutrients were discontinued and the plants were watered daily as needed to prevent wilting. Finally, watering was discontinued when pods began to yellow. Some plants were moved to a greenhouse at flowering; in the greenhouse, the temperature ranged from 20° to 25° C., and the photoperiod was 14:10 hours.

When plants began to flower, they were covered with mesh pollen-containment bags to prevent outcrossing. Self-pollination was facilitated by shaking the plants several times each day. Seeds derived from self-pollinations were harvested about three months after planting.

Minimal A Bacterial Growth Medium

Dissolve in distilled water:
  10.5 g potassium phosphate, dibasic
  4.5 g potassium phosphate, monobasic
  1.0 g ammonium sulfate
  0.5 g sodium citrate, dihydrate
Make up to 979 mLs with distilled water
Autoclave
Add 20 mLs filter-sterilized 10% sucrose
Add 1 mL filter-sterilized 1M $MgSO_4$
Brassica Callus Medium BC-12

Per liter:
  Murashige and Skoog Minimal Organic Medium (MS salts,
  100 mg/L i-inositol, 0.4 mg/L thiamine; GIBCO #510-3118)
  30 g sucrose
  18 g mannitol
  1 mg/L 2,4-D
  3 mg/L kinetin
  0.6% agarose
  pH 5.8
Brassica Regeneration Medium BS-48

Murashige and Skoog Minimal Organic Medium Gamborg B5
Vitamins (SIGMA #G1019)
10 g glucose
250 mg xylose
600 mg MES
0.4% agarose
pH 5.7
Filter-sterilize and add after autoclaving:
  2.0 mg/L zeatin
  0.1% mg/L IAA
Brassica Shoot Elongation Medium MSV-1A Murashige and Skoog Minimal Organic Medium Gamborg B5
Vitamins
10 g sucrose
0.6% agarose
pH 5.8

Table 1 gives an overview over the regenerated plants. A plant was considered sterile if the mature seed harvest totaled less than 40 seeds. *Brassica napus* leaf genomic DNA isolated from transgenic plants (DNA isolation procedure modified from Shure et al., Cell, 35:225-233 (1986)) was analyzed by PCR for the presence of the 10 kD zein coding region using oligonucleotides CW98 and OCW99, which amplify a 212 base pair fragment spanning the amino-terminal half of the 10 kD zein coding region.

OCW98 (SEQ ID NO:8)
5'-CCATTGGGTACCATGAACC-3'

OCW99 (SEQ ID NO:9)
5'-CATCATGCTCGGCAAGACC-3'

TABLE 1

| CW189 β-phaseolin 5'-10 kD zein-β-phaseolin 3' |
| CW190 β-conglycinin 5'-10 kD zein-β-phaseolin 3' |
| CW191 β-conglycinin 5'-SPdel-10 kD zein-β-phaseolin 3' |
| CW192 β-conglycinin 5'-10 kD zein-SEKDEL-β-phaseolin 3' |

| TRANSFORMANT | LINE | GENE | FERTILITY |
| --- | --- | --- | --- |
| CW189- | 1A | + | sterile |
|  | 4 | + | sterile |
|  | 12(2) | + |  |
|  | 52 | + | sterile |
|  | 56 | − |  |
|  | 60 | + |  |
|  | 66(2) | + |  |
| CW190- | 2 | − |  |
|  | 12 | + |  |
|  | 24 | + | sterile |
|  | 34 | − |  |
|  | 43 | + |  |
|  | 57(2) | + |  |
|  | 81 | + |  |
|  | 82 | + | sterile |
|  | 86 | + |  |
|  | 91(2) | + |  |
| CW190- | 92 | + |  |
| CW191- | 2 | − |  |
|  | 5A | + |  |
|  | 6 | + | sterile |
|  | 73 | + | sterile |
| CW192- | 1A | + |  |
|  | 5A | − |  |
|  | 11 | − |  |
|  | 13 | + | sterile |
|  | 14 | + |  |
|  | 19 | + | sterile |
|  | 28 | + |  |
|  | 59 | − |  |
|  | 61 | − |  |
|  | 62 | + |  |
|  | 72 | − |  |
|  | 80 | + |  |
|  | 83 | + |  |
|  | 86 | + |  |
|  | 89B | + | sterile |
|  | 118 | + | sterile |
|  | 119 | − |  |

Example 5

Western Analysis of *Brassica napus* (cv. Westar) Transformant Lines CW 189, CW190, CW191 and CW192

To assay for expression of the chimeric 10 kD zein genes in seeds of transformed *Brassica napus* plants, protein was extracted as follows. Fifteen mature seeds were harvested from each transformant, ground in a mortar with pestel under liquid nitrogen; the fine canola seed meal was transferred to eppendorf tubes and extracted twice with 1 mL of hexane, the solvent clinging to the meal was dried at 65° C. for 10 min. The partially defatted seed meal was extracted once with 300 μL 50 mM Tris-HCl pH 6.8, 2 mM EDTA, 1%

SDS, 1 mM PMSF (TES+P) and spun at 15 krp at room temperature for 5 min. The remaining pellet was extracted twice with 450 μL 70% 2-propanol, 1 mM PMSF, 1% β-mercaptoethanol, the alcohol fractions were combined and dried in a speedvac. The dry pellet was dissolved in 50 μL TES, the protein concentration was determined (BioRad kit, Hercules, Calif.) against BSA as protein standard. Ten μg of total protein were subjected to SDS-PAGE. Proteins were electrophoretically blotted from the gel onto nitrocellulose membrane in a Tris-glycine buffer omitting the methanol. The membranes were incubated with rabbit 10 kD zein-antibodies (see Example 2) at a 1:1000 dilution of the rabbit serum using a standard protocol (BioRad). The secondary antibody was donkey anti-rabbit IgG conjugated to horse-radish peroxidase (Amersham) at a 1:3000 dilution. The specific antibody reaction was visualized by a chemilumi-nescence reaction (Amersham). Both aqueous and alcohol fractions of the extraction of Brassica seed meal of trans-formants was analyzed via Western. 10 kD zein is only present in the alcohol fraction. The signal peptide of 10 kD zein is processed in all cases analyzed so far. The mobility of the 10 kD zein on SDS-polyacrylamide gels is compa-rable to the 10 kD zein overexpressed in E. coli (see Example 2). As estimated from the Western, the expression level of 10 kD zein in the transformants analyzed ranges from 4% of total seed protein for plant CW189-12(2) to less than 0.005% of total seed protein for plant CW192-1A. Table 2 illustrates the results of the Western analysis.

TABLE 2

CW189 β-phaseolin 5'-10 kD zein-phaseolin 3'
CW190 β-conglycinin 5'-10 kD zein-phaseolin 3'
CW191 β-conglycinin 5'-SPdel-10 kD zein-phaseolin 3'
CW192 β-conglycinin 5'-10 kD zein-SEKDEL-phaseolin 3'

| TRANSFORMANT | LINE | WESTERN |
|---|---|---|
| CW189- | 12(2) | +++++ |
| | 60 | +++ |
| | 66(2) | +++ |
| CW190- | 12 | +++++ |
| | 43 | − |
| | 57(2) | +++++ |
| | 81 | ++++ |
| | 86 | ++++ |
| CW190- | 91(2) | ++++ |
| | 92 | ++++ |
| CW191- | 5A | ++ |
| CW192- | 1A | +++ |
| | 14 | ++ |
| | 28 | +++ |
| | 62 | ++ |
| | 80 | ++ |
| | 83 | ++ |

TABLE 2-continued

CW189 β-phaseolin 5'-10 kD zein-phaseolin 3'
CW190 β-conglycinin 5'-10 kD zein-phaseolin 3'
CW191 β-conglycinin 5'-SPdel-10 kD zein-phaseolin 3'
CW192 β-conglycinin 5'-10 kD zein-SEKDEL-phaseolin 3'

| TRANSFORMANT | LINE | WESTERN |
|---|---|---|
| | 86 | +++ |
| | 118 | ++ |
| | 119 | nd |

Example 6

Amino Acid Analysis of Brassica napus (cv. Westar) Transformants CW189-12(2)

Figure 3:
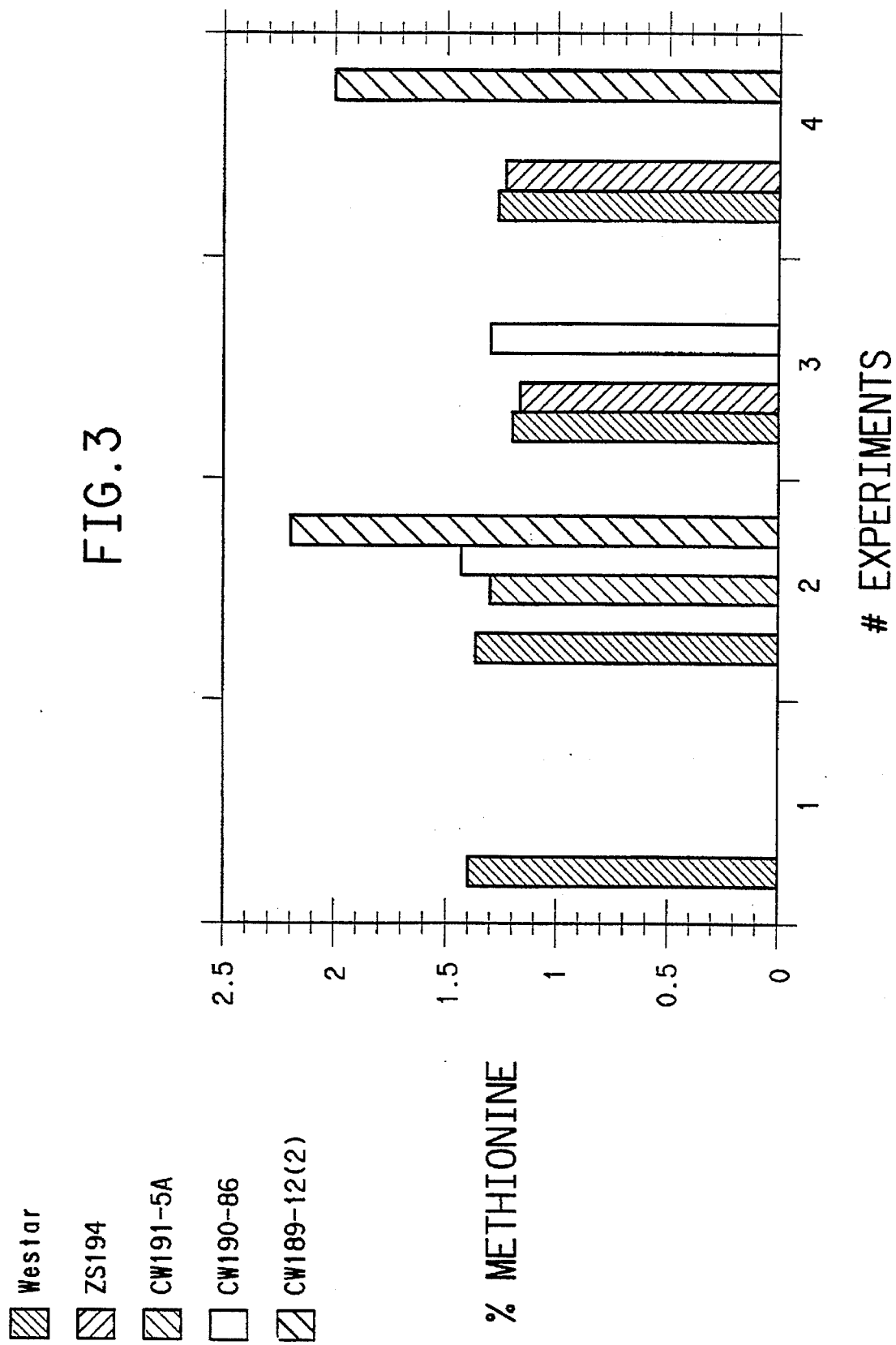
FIG. 3 shows the results of the amino acid analysis of mature seeds of transformed *Brassica napus* plants.
Figure 4:
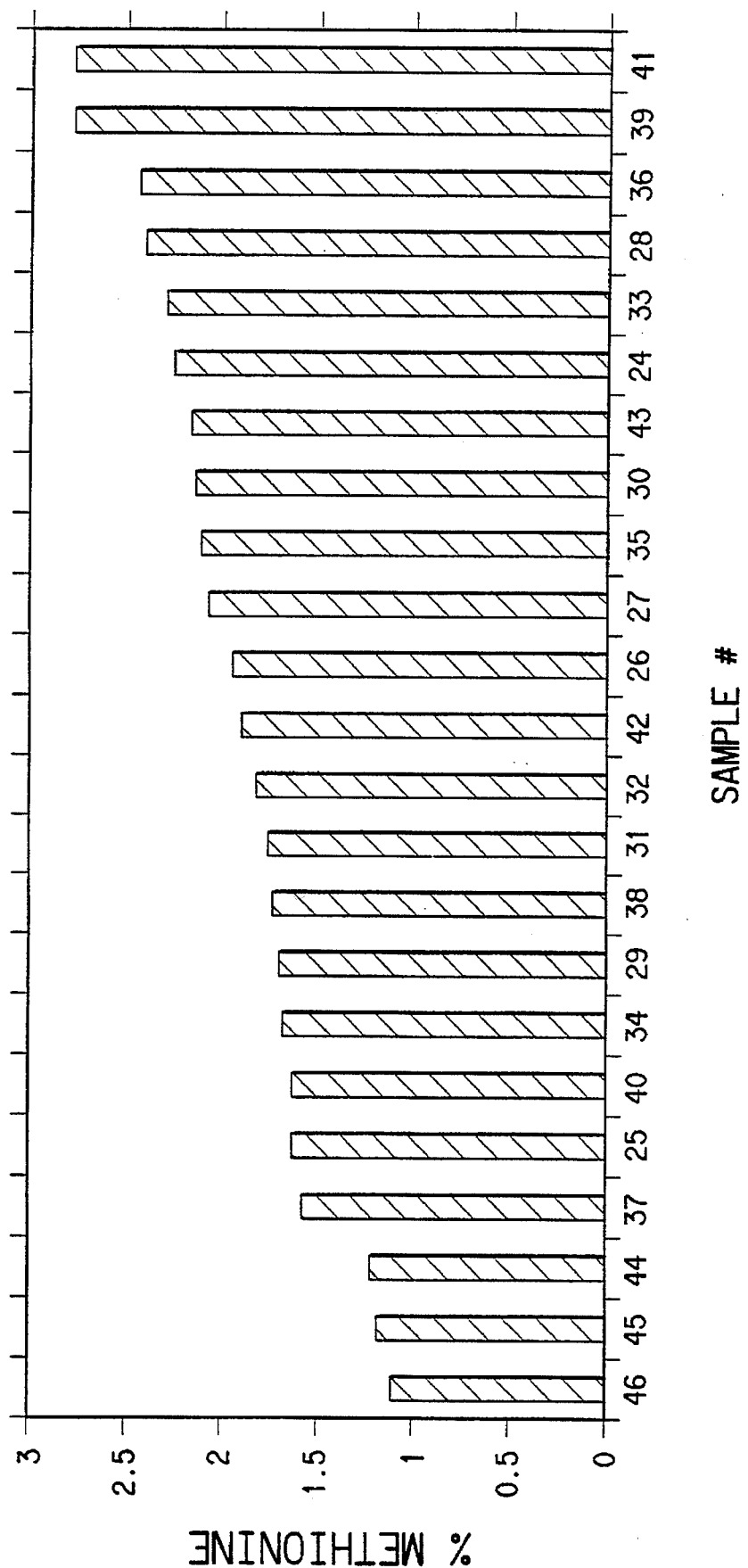
FIG. 4 presents the results of a single seed amino acid analysis of transgenic *Brassica napus* plant CW189-12(2).

To measure the amino acid composition of mature trans-genic brassica seeds, (1) 15 mature seeds were ground to a fine powder under liquid nitrogen in a mortar with pestel and hexane extracted twice; approximately two milligrams of partially defatted canola seed meal was subjected to amino acid analysis, or (2) one single mature seed (approx. 5 mg) was crashed and subjected to amino acid analysis: the samples were hydrolyzed in 6 N hydrochloric acid, 0.4% β-mercaptoethanol under nitrogen for 24 h at 110°–120° C.; aliquots of samples (1) or (2) were run on a Beckman Model 6300 amino acid analyzer using post-column ninhydrin detection. The amino acid analysis results of analyzed transgenic plants are shown in FIGS. 3 and 4. Values are given as percent methionine of all amino acids analyzed (excluding cysteine and tryptophane).

Table 3 gives the results of the amino acid analysis of the control plants Westar and ZS194, a binary vector-only canola transformant (refer to binary Ti plasmid based vec-tors described in Example 3), and CW189-12(2), the highest expressing canola transformant for 10 kD zein. As indicated by A, B or C (column 1), 15 individual seeds from one transformant were ground to seed meal, defatted and ana-lyzed as described above. Given are the values (columns 3 and 4), the mean and standard deviation (columns 5 and 6) for three aliquots (column 2) of the same seed meal batch. The methionine content is expressed as mole (column 3) and grams per 100 grams seed meal (column 4). Given as well are the total amino acid yields in μmole (column 8), exclud-ing tryptophane and cysteine, and based on that the calcu-lated amount of extracted protein (column 9). Columns 10 and 11 illustrate the efficiency of the extraction based on the expected protein content of canola meal of 37%.

TABLE 3

| Line | mg Seed Meal Per Analysis | nmole Methionine | Grams Methionine per 100 g Seed Meal | Mean (std dev) | Mean (std dev) |
|---|---|---|---|---|---|
| Westar C | 1.7 | 40.53 | 0.36 | 0.41 (0.05) | 0.41(0.05) |
| | 1.1 | 31.07 | 0.42 | | |
| | 1.4 | 43 | 0.46 | | |
| ZS194 A | 1.3 | 39.78 | 0.46 | 0.45 (0.02) | 0.47(0.03) |
| | 1.2 | 37.09 | 0.46 | | |
| | 1.7 | 49.11 | 0.43 | | |
| ZS194 B | 1.5 | 44.78 | 0.45 | 0.49 (0.04) | |
| | 1 | 33.96 | 0.51 | | |
| | 1 | 34.68 | 0.52 | | |
| CW189-12(2) A | 1.7 | 77.63 | 0.68 | 0.78 (0.09) | 0.83(0.12) |

TABLE 3-continued

| Line | | | | | |
|---|---|---|---|---|---|
| | 1.5 | 82.03 | 0.82 | | |
| | 1.3 | 73.18 | 0.84 | | |
| CW189-12(2) B | 1.6 | 65.41 | 0.61 | 0.75 (0.12) | |
| | 1.4 | 78.34 | 0.83 | | |
| | 1.8 | 98.04 | 0.81 | | |
| CW189-12(2) C | 1.5 | 110 | 1.09 | 0.97 (0.11) | |
| | 1.1 | 67.66 | 0.92 | | |
| | 1.3 | 77.35 | 0.89 | | |

| Line | % Increase in Total Seed Methionine | Total µmole Amino Acids Minus trp, cys | % Protein Extracted from Seed Meal | % of 37% of Extractable Protein | Mean (std dev) |
|---|---|---|---|---|---|
| Westar C | 0 | 3.4 | 23 | 62 | 69(8) |
| | | 2.4 | 25 | 68 | |
| | | 3.5 | 29 | 78 | |
| ZS194 A | 15 | 3.3 | 29 | 79 | 80(2) |
| | | 3.2 | 31 | 83 | |
| | | 4.3 | 29 | 79 | |
| ZS194 B | 3.8 | 29 | 79 | 85(6) | |
| | | 2.8 | 32 | 87 | |
| | | 2.9 | 33 | 90 | |
| CW189-12(2) A | 102 | 4 | 27 | 73 | 86(12) |
| | | 4.3 | 33 | 89 | |
| | | 4 | 35 | 96 | |
| CW189-12(2) B | 4.2 | 30 | 82 | 85(4) | |
| | | 3.8 | 31 | 84 | |
| | | 5.2 | 33 | 90 | |
| CW189-12(2) C | | 5.2 | 40 | 108 | 99(8) |
| | | 3.4 | 36 | 96 | |
| | | 3.9 | 35 | 93 | |

The methionine content of *Brassica napus* (cv. Westar) is described in the literature as 0.76 grams per 100 grams defatted seed meal. The methionine values obtained and described in this invention are the values based on the amino acid analysis method given in this example and based on the growth conditions (see Example 4) of the analyzed transformed plants. Given in Example 5 is the expression level of 10 kD zein in plant CW189-12(2) as approximately 4% 10 kD zein of total extractable seed protein. One can calculate as shown in Table 5 the expected increase in total seed methionine, based on this expression level and the mole percent methionine of the mature 10 kD zein protein (see Table 4).

TABLE 4

Amino Acid Composition of Mature 10 kD Zein Polypeptide

| Residue | Number | Mole Percent |
|---|---|---|
| Alanine | 7 | 5.4 |
| Cysteine | 5 | 3.9 |
| Aspartic acid | 1 | 0.8 |
| Phenylalanine | 5 | 3.9 |
| Glycine | 4 | 3.1 |
| Histidine | 3 | 2.3 |
| Isoleucine | 4 | 3.1 |
| Leucine | 15 | 11.6 |
| Methionine | 28 | 21.7 |
| Asparagine | 3 | 2.3 |
| Proline | 20 | 15.5 |
| Glutamine | 15 | 11.6 |
| Serine | 8 | 6.2 |
| Threonine | 5 | 3.9 |
| Valine | 5 | 3.9 |
| Tyrosine | 1 | 0.8 |
| Total | 129 | 100 |

TABLE 5

| Grams Methionione per 100 grams of seed meal | % 10 kD Zein of Total Seed Protein | % Increase in Total Seed Methionine |
|---|---|---|
| 0.76 | 0 | 0 |
| 1.20 | 2 | 58 |
| 1.64 | 4 | 116 |
| 2.08 | 6 | 174 |
| 2.52 | 8 | 232 |

As shown in Table 3, column 7, the increase in total seed methionine for transformant CW189-12(2) of 102% is in good agreement with the calculated 116% increase in total seed methionine (given in Table 5) based on the literature value for a total canola seed meal methionine content of 0.76 g methionine per 100 g of seed meal.

The single seed analysis shown in FIG. 4 shows part of the possible range of total seed methionine levels (expressed as % methionine of analyzed amino acids) in a segregating seed population of 20 seeds from the transgenic canola plant CW189-12(2). One can envision based on the values given in Table 5 that in a progeny plant homozygous for the 10 kD zein gene(s) the total seed methionine increase will be as high as 232% assuming an expression of the 10 kD zein at levels of 8% of total seed protein.

Example 7

Southern Analysis of *Brassica napus* (cv. Westar) Transformant CW189-12(2)

Figure 5:
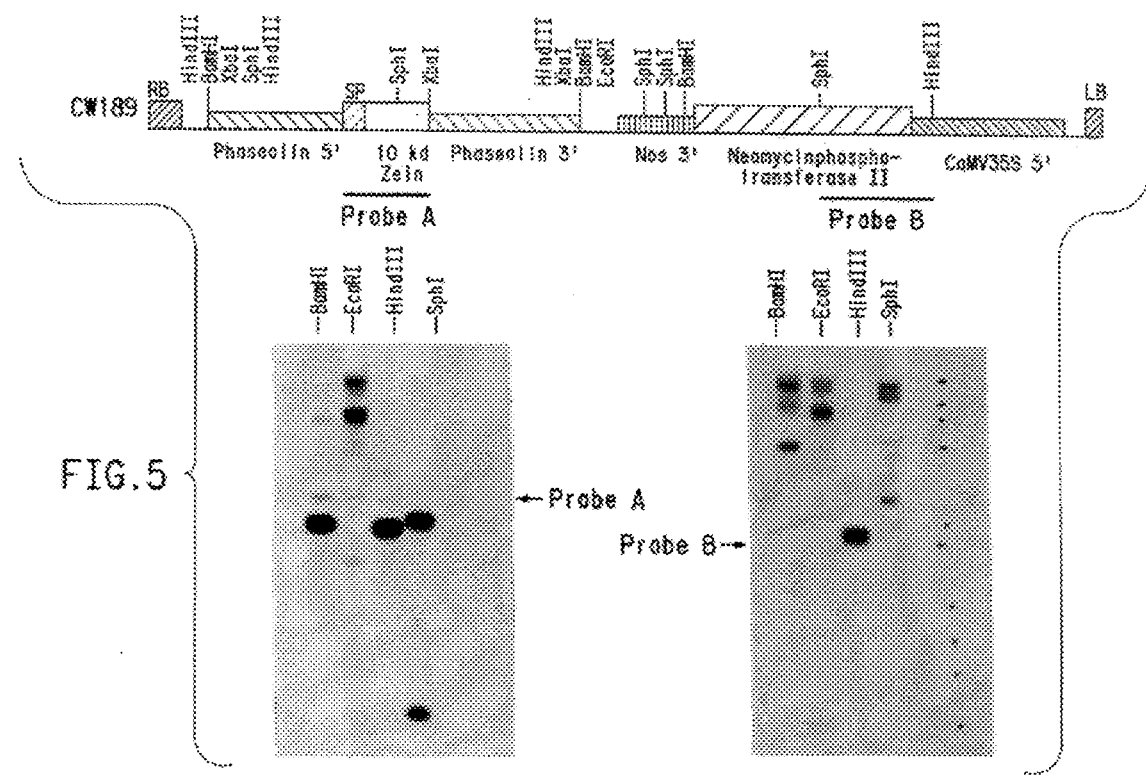
FIG. 5 presents the results of a Southern analysis described in Example 7.

Genomic DNA was extracted from *Brassica napus* transformant leaves (see also Example 4), digested with HindIII, EcoRI, BamHI and XbaI or SpHI to completion and separated on an agarose gel and transfered onto a membrane (Amersham Hybond N). The blot was probed with DNA fragments representing the 10 kD zein chimeric gone or the selectable marker gene (Random-Primed Labeling kit from Boehringer Mannheim: hybridization following Khandjian, Bio/Technol., 5:165-167 (1987)). FIG. 5 shows the gene structure of CW189 and the Southern data obtained for plant CW189-12(2). Segregation analysis for the marker gene neomycin phosphotransferase II indicated two single loci of insertion for the selectable marker gene. The complex banding pattern for plant CW189-12(2) indicated, that there are at least 2 major loci with multiple tandem insertions of the 10 kD zein gene, rearrangements and deletions. In part, the tandem insertions and most likely the multiple copies are the cause of this plant being a high expressor. The copy number for the 10 kD zein gene in plant CW189-12(2) is estimated at approximately 25.

Example 8

Transformation of Soybean with a β-Phaseolin-10 kD Zein Chimeric Gene

To induce somatic embryos, cotyledons, 4–5 mm in length dissected from surface sterilized, immature seeds of soybean, were cultured in the dark at 25° C. on an agar medium (SB1 or SB2) for 8–10 weeks. Somatic embryos, which produce secondary embryos were excised and placed into a liquid medium (SB55). After repeated selection for clusters of somatic embryos which multiply as early, globular staged embryos, the suspensions were maintained as described below.

Soybean embryogenic suspension cultures were maintained in 35 mL liquid media (SB55) on a rotary shaker, 150 rpm, at 28° C. with mixed florescent and incandescent lights on a 16:8 hour day/night schedule. Cultures were subcultured every two weeks.

Soybean embryogenic suspension cultures were transformed by the method of particle gun bombardment (Klein et al. (1987) Nature (London) 327:70, U.S. Pat. No. 4,945, 050). A Du Pont Biolistic, PDS1000/HE instrument (helium retrofit) was used for these transformations.

The plasmid vector used for transformation will be a derivative of pGEM9Z (Promega Biological Research Products). As a selectable marker a chimeric gene composed of the 35S promoter from Cauliflower Mosaic Virus [Odell et al. (1985) Nature 313:810–812], the hygromycin phosphotransferase (hygro)gene from plasmid pJR225 (from *E. coli*) [Gritz et al. (1983) Gene 25:179–188] and the 3' region of the nopaline synthase gene from the T-DNA of the Ti plasmid of *Agrobacterium tumefaciens* (see SEQ ID NO:26 in BB-1027-A) was at the Sal I site of the vector. The β-phaseolin-10 kD zein chimeric gene cassette, β-phaseolin 5' region/10 kD zein/β-phaseolin 3' region, (see pCW126 in Example 3) was isolated as an approximately 2.2 kb Hind III fragment. This fragment was inserted into the unique Hind III site of the vector resulting in plasmid pCW157.

To 50 µL of a 60 mg/mL 1 mm gold particle suspension the following were added (in order); 5 µL DNA(1 µg/µL), 20 µl spermidine (0.1M), and 50 µL CaCl₂ (2.5M). The particle preparation was agitated for three minutes, spun in a microfuge for 10 seconds and the supernatant was removed. The DNA-coated particles were washed once in 400 µL 70% ethanol and resuspended in 40 µL of anhydrous ethanol. The DNA/particle suspension was sonicated three times for one second each. Five µL of the DNA-coated gold particles were be loaded on each macro carrier disk.

Approximately 400–800 mg of a two-week-old suspension culture were placed in an empty 60×15 mm petri dish and the residual liquid removed from the tissue with a pipette. For each transformation experiment, approximately 5–10 plates of tissue were normally bombarded. Membrane rupture pressure was set at 1000 psi and the chamber was evacuated to a vacuum of 28 inches mercury. The tissue was placed approximately 3.5 inches away from the retaining screen and bombarded three times. Following bombardment, the tissue was placed back into liquid and cultured as described above.

Seven to fourteen days post bombardment, the liquid media will be exchanged with fresh SB55 containing 50 mg/mL hygromycin. The selective media will be refreshed weekly. Five to seven weeks post bombardment, green, transformed tissue will be observed growing from untransformed, necrotic embryogenic clusters. Isolated green tissue will be removed and inoculated into multiwell plates to generate new, clonally propagated, transformed embryogenic suspension cultures. Thus each new line will be treated as an independent transformation event. These suspensions can then be subcultured and maintained as clusters of immature embryos or regenerated into whole plants by maturation and germination of individual somatic embryos.

Transformed embryogenic clusters are removed from liquid culture and placed on a solid agar media (SB 103) containing no hormones or antibiotics. Embryos are cultured for eight weeks at 26° C. with mixed florescent and incandescent lights on a 16:8 hour day/night schedule. During this period, individual embryos will be removed from the clusters and analyzed for production of the 10 kD zein protein as described below. After eight weeks, the embryos are suitable for germination.

Individual embryos are frozen in liquid nitrogen, and ground to a fine powder with a morter and pestle prechilled in liquid nitrogen. The powder is scraped into an eppendorf centrifuge tube and extracted twice with hexane at room temperature. The residue is incubated at 60° C. for 30 min to allow residual hexane to evaporate. Then 100 µL of 50 mM Tris-HCl pH 6.7, 2 mM EDTA, 1% SDS 1% beta-mercaptoethanol (TESµ) is added to the pellet and it is ground at low speed for about 10 sec using a motorized grinder with disposable plastic shafts designed to fit into the microfuge tube. The resultant suspensions are centrifuged for 5 min at room temperature in a microfuge and the supernatant is removed and saved. The pellet is resuspended in 50 µL of 70% isopropanol, 10 mM β-mercaptoethanol by grinding as above. The tube is incubated at 60° C. for 5 min and centrifuged as above. The supernatant is saved and the pellet extracted again with 50 µL of 70% isopropanol, 10 mM µ-mercaptoethanol. The alcohol extracts are pooled and lyophilized; the residue is resuspended in 50 µL of TESµ. This sample and the first TESµ extract is assayed for the presence of 10 kD zein protein by Western blot as described in Example 5.

Media:

SB55 Stock Solutions (grams per liter):

| MS Sulfate 100X Stock | | MS Halides 100X Stock | |
|---|---|---|---|
| MgSO₄ 7 H₂O | 37.0, | CaCl₂ 2 H₂O | 44.0, |

-continued

| | | | |
|---|---|---|---|
| MnSO₄ H₂O | 1.69, | KI | 0.083, |
| ZnSO₄ 7 H₂O | 0.86, | CoCl₂ 6 H₂O | 0.00125 |
| CuSO₄ 5 H₂O | 0.0025 | | |

MS P,B,Mo 100X Stock

MS FEEDTA 100X Stock

| | | | |
|---|---|---|---|
| KH₂PO₄ | 17.0, | Na₂EDTA | 3.724, |
| H₃BO₃ | 0.62, | FeSO₄ 7 H₂O | 2.784 |
| Na₂MoO₄ 2 H₂O | 0.025 | | |

B5 Vitamin Stock

SB55 (per liter)

10 g m-inositol,
100 mg nicotinic acid.
100 mg pyridoxine HCl,
1 g thiamine 10 mL each MS stocks,
1 mL B5 Vitamin stock
0.8 g NH₄NO₃
3.033 g KNO₃
1 mL 2,4-D (10 mg/ml stock)
60 g sucrose
0.667 g asparagine
pH 5.7

SB103 (per liter)

SB1 (per liter)

MS Salts
6% maltose
750 mg MgCl₂
0.2% GELRITE
pH 5.7 0.8% agar

MS Salts
B5 Vitamins
0.175 M glucose
20 mg 2,4-D pH 5.8

SB2 same as SB 1 except 40 mg/L 2,4-D

---

What is claimed is:

1. A chimeric gene comprising the following elements operably linked in a 5' to 3' orientation; (a) a dicotyledonous seed-specific promoter, (b) an intracellular localization sequence, (c) the maize 10 kD zein coding region, and (d) a 3' non-coding sequence, wherein said chimeric gene causes an increase in total seed methionine in plant cells in which the gene is expressed as compared to untransformed plant cells.

2. The chimeric gene of claim 1 wherein the seed-specific promoter is the bean β-phaseolin promoter.

3. The chimeric gene of claim 2 wherein the bean beta-phaseolin promoter comprises, operably linked in a 5' to 3' direction, 410 bp of sequence located immediately upstream of the transcription initiation site, and the 5' transcribed but untranslated leader sequence.

4. The chimeric gene of claim 1 wherein the 3' non-coding sequence is bean β-phaseolin 3' non-coding sequence.

5. The chimeric gene of claim 1 wherein the intracellular localization sequence is an amino-terminal signal peptide sequence.

6. The chimeric gene of claim 5 wherein the intracellular localization sequence is the 10 kD zein amino-terminal signal peptide sequence.

7. A dicotyledonous plant transformed with a chimeric gene comprising the following elements operably linked in a 5' to 3' orientation; (a) a dicotyledonous seed-specific promoter, (b) an intracellular localization sequence, (c) the maize 10 kD zein coding region, and (d) a 3' non-coding sequence, wherein said chimeric gene causes an increase in total seed methionine in plant cells in which the gene is expressed as compared to untransformed plant cells.

8. The transformed dicotyledonous plant of claim 7 wherein the plant is rapeseed.

9. The transformed dicotyledonous plant of claim 7 wherein the plant is soybean.

10. Seed obtained from the plant of claim 7.

11. A plant according to claim 7 comprising multiple copies of the chimeric gene inserted in its genome.

12. A method of increasing the sulfur amino acid content of a dicotyledonous plant comprising:
  (a) transforming a dicotyledonous plant cell with a chimeric gene comprising the following elements operably linked in a 5' to 3' orientation; (a) a dicotyledonous seed-specific promoter, (b) an intracellular localization sequence, (c) the maize 10kD zein coding region, and (d) a 3' non-coding sequence;
  (b) selecting transformed plant cells from step (a) on the basis of a selectable marker;
  (c) growing fertile, sexually mature plants from the selected transformed plant cell of step (b); and
  (d) selecting progeny seed from the fertile plants of step (b) for increased levels of total seed methionine relative to dicotyledonous plant cells of the same type as those transformed in step (a) but not containing the chimeric gene.

13. A method according to claim 12 wherein the plant is rapeseed and the increase in total seed methionine is between 29% and 232% as compared with a *Brassica napus* (cv. Westar) untransformed control, which has 0.76 grams methionine per 100 grams of defatted seed meal.

14. A method according to claim 12 wherein the plant is rapeseed and the seeds contain between 1% and 8% of total extractable seed protein as 10 kD zein.

15. Components of seeds obtained from the plant of claim 7 selected from the group consisting of embryo, seed endosperm and seed coat.

16. A method of increasing the methionine content of soybean or rapeseed plants comprising:
  (a) transforming a soybean or rapeseed plant cell with a chimeric gene comprising the following elements operably linked in a 5' to 3' orientation; (a) a dicotyledonous seed-specific promoter, (b) an intracellular localization sequence, (c) the maize 10kD zein coding region, and (d) a 3' non-coding sequence;
  (b) selecting transformed plant cells from step (a) on the basis of a selectable marker;
  (c) growing fertile, sexually mature plants from the selected transformed plant cell of step (b); and
  (d) selecting progeny seed from the fertile plants of step (b) for increased levels of total seed methionine relative to soybean or rapeseed plant cells of the same type as those transformed in step (a) but not containing the chimeric gene.

* * * * *

(12) REEXAMINATION CERTIFICATE (4263rd)
United States Patent
Wandelt

(10) Number: US 5,633,436 C1
(45) Certificate Issued: Jan. 30, 2001

(54) FEEDCROPS ENRICHED IN SULFUR AMINO ACIDS AND METHODS FOR IMPROVEMENTS

(75) Inventor: Christine I. Wandelt, Ardentown, DE (US)

(73) Assignee: E. I. du Pont de Nemours and Company, Willmington, DE (US)

Reexamination Request:
No. 90/005,291, Mar. 15, 1999

Reexamination Certificate for:
Patent No.: 5,633,436
Issued: May 27, 1997
Appl. No.: 08/321,080
Filed: Oct. 11, 1994

Related U.S. Application Data

(63) Continuation of application No. 08/129,721, filed on Sep. 30, 1993, now abandoned, which is a continuation-in-part of application No. 08/029,339, filed on Mar. 2, 1993, now abandoned.

(51) Int. Cl.⁷ .............................. A01H 5/00; C12N 15/29; C12N 15/82
(52) U.S. Cl. ................ 800/267; 800/293; 800/306; 536/23.6; 536/24.1; 435/69.1; 435/320.1; 435/415; 435/419
(58) Field of Search ................. 536/23.6, 24.1; 435/69.1, 320.1, 415, 419, 468; 800/278, 287, 298

(56) References Cited

PUBLICATIONS

Park, Jee Won et al., Promoter Sequence of Soybean Glycinin Gene Regulates Seed–Specific Expression in Transgenic Tobacco Plant, *Mol. Cells,* 2, 297–302, 1992.

*Primary Examiner*—Elizabeth F. McElwain

(57) ABSTRACT

There is provided a chimeric gene and a method to increase the seed methionine content in plants. The chimeric gene is capable of transforming plants, particularly rapeseed and soybean, to overexpress a methionine-rich maize seed storage protein in seeds. There is also provided the plants and seeds containing the chimeric gene.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–16 is confirmed.

* * * * *